United States Patent
Jahangir

(10) Patent No.: US 6,417,186 B1
(45) Date of Patent: Jul. 9, 2002

(54) SUBSTITUTED-PHENYL KETONE DERIVATIVES AS IP ANTAGONISTS

(75) Inventor: Alam Jahangir, San Jose, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/014,110

(22) Filed: Nov. 13, 2001

Related U.S. Application Data

(60) Provisional application No. 60/248,888, filed on Nov. 14, 2000.

(51) Int. Cl.$^7$ ............................................. A61K 31/535
(52) U.S. Cl. .................... 514/235.8; 544/139; 544/366; 548/333.1; 514/401; 514/254.05
(58) Field of Search ........................ 548/333.1; 514/401, 514/402, 235.8, 254.05; 544/139, 366

(56) References Cited

U.S. PATENT DOCUMENTS

| | | |
|---|---|---|
| 3,931,216 A | 1/1976 | Franzmair |
| 4,287,201 A | 9/1981 | Olson et al. |
| 4,374,143 A | 2/1983 | Dolman et al. |
| 4,396,617 A | 8/1983 | Dolman et al. |
| 4,588,737 A | 5/1986 | Huang |
| 4,889,868 A | 12/1989 | Huang |
| 5,218,124 A | 6/1993 | Failli et al. |
| 5,326,776 A | 7/1994 | Winn et al. |
| 5,364,944 A | 11/1994 | Failli et al. |
| 6,184,242 B1 | 2/2001 | Bley et al. |

FOREIGN PATENT DOCUMENTS

| | | |
|---|---|---|
| EP | 0 017 484 A1 | 10/1980 |
| GB | 2 038 305 A | 7/1980 |

OTHER PUBLICATIONS

Srivastava, et al, "1–[4(4, 5–Dihydro–1H–imidazol–2–yl)aminophenyl]–3–(substituted phenyl)–2–propene–1–one as Antiparkinsonian Agents", Pharmazie, 1986, pp. 598–599, 41.

Bley et al., "The role of IP prostanoid receptors in inflammatory pain", Trends in Pharmacological Sciences, 1998, pp. 141–147, 19 (4), #98275036.

Smith et al., "Characterization of prostanoid receptor–evoked responses in rat sensory neurones", British Journal of Pharmacology, 1998, pp. 513–523, 124(3).

Murata et al., "Altered pain perception and inflammatory response in mice lacking prostacyclin receptor," Nature, 1997, pp. 678–682, 388 (6643).

Anderson, "Pharmacology of Lower Urinary Tract Smooth Muscles and Penil Erectile Tissues", Pharmacological Reviews, 1993, pp. 253–308, 45 (3).

Coleman et al., "VIII. International Union of Pharmacology Classification of Prostanoid Receptors: Properties, Distribution, and Structure of the Receptors and Their Subtypes", Pharmacological Review, 1994, pp. 205–229, 46(2).

*Primary Examiner*—Joseph K. McKane
*Assistant Examiner*—Rebecca Anderson
(74) *Attorney, Agent, or Firm*—Gloria Pfister

(57) ABSTRACT

This invention relates to compounds which are generally IP receptor modulators, particularly IP receptor antagonists, and which are represented by Formula I:

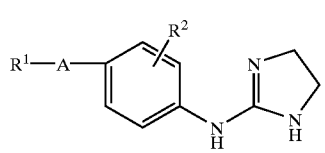

(I)

wherein A, $R^1$ and $R^2$ are as defined in the specification; and individual isomers, racemic or non-racemic mixtures of isomers, and pharmaceutically acceptable salts or solvates thereof. The invention further relates to pharmaceutical compositions containing such compounds and methods for their use as therapeutic agents.

29 Claims, No Drawings

SUBSTITUTED-PHENYL KETONE DERIVATIVES AS IP ANTAGONISTS

CROSS-REFERENCE TO RELATED APPLICATION

This application claims benefit under Title 35 U.S.C. 119(e) of U.S. Provisional Application No. 60/248,888 filed Nov. 14, 2000.

BACKGROUND OF THE INVENTION

1. Field of the Invention

This invention relates to certain substituted-phenyl ketone derivatives as prostaglandin $I_2$ (IP) receptor antagonists, and associated pharmaceutical compositions containing them, and methods for their use as therapeutic agents.

2. Background of the Invention

Prostaglandins or prostanoids (PG's) are a group of bioactive compounds derived from membrane phospholipids and are formed from 20-carbon essential fatty acids containing three, four, or five double bonds, and a cyclopentane ring. They fall into several main classes designated by the letters D, E, F, G, H, or I, and are distinguished by substitutions to the cyclopentane ring. The main classes are further subdivided by subscripts 1, 2, or 3, which reflect their fatty acid precursors. Thus, $PGI_2$ has a double ring structure, and the subscript 2 indicates that it is related to arachidonic acid.

$PGI_2$ (also known as prostacyclin) acts on platelets and blood vessels to inhibit aggregation and to cause vasodilation, and is thought to be important for vascular homeostasis. It has been suggested that $PGI_2$ may contribute to the antithrombogenic properties of the intact vascular wall. $PGI_2$ is also thought to be a physiological modulator of vascular tone that functions to oppose the actions of vasoconstrictors. The importance of these vascular actions is emphasized by the participation of $PGI_2$ in the hypotension associated with septic shock. Although prostaglandins do not appear to have direct effects on vascular permeability, $PGI_2$ markedly enhances edema formation and leukocyte infiltration by promoting blood flow in the inflamed region. Therefore, IP receptor antagonists may relieve hypotension related to septic shock, may reduce edema formation, and may prevent conditions associated with excessive bleeding such as, but not limited to, hemophilia and hemorrhaging.

Several in vivo analgesia studies in rodents suggest that $PGI_2$ plays a major role in the induction of hyperalgesia. Likewise, in vitro studies provide substantial evidence to suggest that "$PGI_2$-preferring" (IP) receptors act as important modulators of sensory neuron function (K. Bley et al, *Trends in Pharmacological Sciences* 1998, 19(4):141–147). Since IP receptors in sensory neurons are coupled to activation of both adenylyl cyclase and phospholipase C, and hence, cAMP-dependent protein kinase and protein kinase C, these receptors can exert powerful effects on ion channel activity and thus neurotransmitter release. Evidence of a prominent role for IP receptors in inflammatory pain has been obtained from recent studies in transgenic mice lacking the IP receptor (T. Murata et al., *Nature* 1997, 388, 678–682).

In addition to being mediators of hyperalgesia, prostaglandins are known to be generated locally in the bladder in response to physiologic stimuli such as stretch of the detrusor smooth muscle, injuries of the vesical mucosa, and nerve stimulation (K. Anderson, *Pharmacological Reviews* 1993, 45(3), 253–308). $PGI_2$ is the major prostaglandin released from the human bladder. There are suggestions that prostaglandins may be the link between detrusor muscle stretch produced by bladder filling and activation of C-fiber afferents by bladder distension. It has been proposed that prostaglandins may be involved in the pathophysiology of bladder disorders. Therefore, antagonists of prostaglandin IP receptors are expected to be useful in the treatment of such conditions.

Antagonists of IP receptors are also expected to find a utility in respiratory allergies wherein $PGI_2$ production in response to an allergen is present or in respiratory conditions such as asthma.

Additional information relating to prostaglandins and their receptors is described in *Goodman & Gillman's, The Pharmacological Basis of Therapeutics*, ninth edition, McGraw-Hill, New York, 1996, Chapter 26, pages 601–616.

DESCRIPTION OF THE RELATED ART

U.S. Pat. No. 6,184,242 (Bley et al.) refer to certain 2-(substituted-phenyl)amino imidazoline derivatives.

U.S. Patent Nos. 5,364,944 and 5,218,124 (Failli et al.) refer to certain substituted benzoylbenzene-, biphenyl-, and 2-oxazole-alkanoic acid derivatives which are disclosed as having lipoxygenase inhibitory, phospholipase A2 inhibitory, and leukotriene antagonist activity, which are useful as anti-inflammatory, anti-allergic, and cytoprotective agents.

U.S. Pat. No. 5,326,776 (Winn et al.) refers to certain substituted phenyl derivatives which are disclosed as angiotensin II receptor antagonists useful for treating hypertension, edema, renal failure, benign prostatic hypertrophy, diabetic nephropathy, diabetic retinopathy, Alzheimer's disease or congestive heart failure, glaucoma, atherosclerosis, stroke, a variety of obesity-related disorders, and CNS disorders.

U.S. Pat. Nos. 4,889,868 and 4,588,737 (Huang) refer to certain bis-imidazolinoamino derivatives which are disclosed as lipoxygenase and phospholipase C inhibitors and platelet-activating factor receptor antagonists which possess anti-inflammatory, anti-asthmatic, and anti-allergic properties and are additionally useful for treating myocardial infarctions.

U.S. Pat. Nos. 4,396,617 and 4,374,143 (Dolman and Kuipers) refer to certain 2-arylimino-imidazolidines which are disclosed as being fungicides active against rust of beans, brown rust of wheat and mildew on cereals.

U.S. Pat. No. 4,287,201 (Olson et al.) refers to certain 2-(substituted phenylimino)imidazolidine derivatives which are disclosed as being useful in delaying the onset of egg production in young pullets, interrupting egg production in mature hens, and in producing an artificial molt.

U.S. Pat. No. 3,931,216 (Franzmair) refers to a process for the preparation of 2-arylamino-2-imidazoline derivatives.

British Patent Application No. GB 2 038 305 (assigned to Duphar International Research) refers to certain imidazolidine compounds which are disclosed as inhibiting growth of side shoots tobacco or tomato plants, or inhibiting lawn growth, or dwarf ornamental plants.

European Published Application No. 0 017 484 (assigned to Fujisawa Pharmaceutical) refers to certain 2-imidazoline derivatives which are disclosed as being useful for the treatment of hypertensive, inflammatory and gastrointestinal disorder and relief from pain of various origins.

Srivastava, V. K. et al., *Pharmazie* 1986, 41, 598–599, refers to certain 1-[4-(4,5-dihydro-1H-imidazol-2-yl)

aminophenyl]-3-substituted phenyl)-2-propene-1-one derivatives which are disclosed as antiparkinsonian agents.

Bley et al., *Trends in Pharmacological Sciences* 1998, 19 (4), 141–147 refers to the role of IP prostanoid receptors in inflammatory pain.

Smith et al., *British Journal of Pharmacology* 1998, 124(3), 513–523 refers to the characterization of prostanoid receptor-evoked responses in rat sensory neurons.

Murata et al., *Nature* 1997, 388 (6643), 678–682 refers to altered pain perception and inflammatory response in mice lacking prostacyclin receptors.

Anderson, K-E., *Pharmacological Reviews* 1993, 45(3), 253–308 refers to the pharmacology of lower urinary tract smooth muscles and penile erectile tissues.

Coleman et al, *Pharmacological Review* 1994, 46(2), 205–229 refers to the classification of prostanoid receptors: properties, distribution and structure of prostanoid receptors and their subtypes.

All publications, patents, and patent applications cited herein, whether supra or infra, are each hereby incorporated by reference in its entirety.

SUMMARY OF THE INVENTION

This invention relates to compounds comprising Formula I:

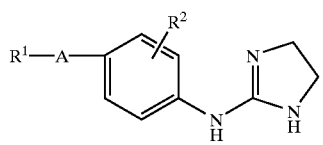

(I)

wherein:

$R^1$ is an optionally substituted aryl; wherein $R^1$ is optionally substituted by one, two, or three substituents independently selected from lower alkyl, alkoxy, aryloxy, aralkyloxy, halogen, haloalkyl, hydroxy, hydroxyalkyl, nitro, cycloalkyl, amino, alkylamino, dialkylamino, methylenedioxy, ethylenedioxy, and optionally substituted heterocyclyl;

$R^2$ is hydrogen, lower alkyl, or halogen;

A is —C(O)—(CH$_2$)$_n$— or —C(O)CH$_2$O—; and the subscript n is an integer from 2 to 6 inclusive; or individual isomers, racemic or non-racemic mixtures of isomers, or pharmaceutically acceptable salts or solvates thereof.

This invention further relates to pharmaceutical compositions comprising a therapeutically effective amount of at least one compound of Formula I, or individual isomers, racemic or non-racemic mixtures of isomers, or pharmaceutically acceptable salts or solvates thereof, in admixture with at least one suitable carrier. In a preferred embodiment, the pharmaceutical compositions are suitable for administration to a subject having a disease state that is alleviated by treatment with an IP receptor antagonist.

This invention further relates to methods of treatment comprising administering to a subject in need of such treatment a therapeutically effective amount of at least one compound of Formula I, or individual isomers, racemic or non-racemic mixtures of isomers, or pharmaceutically acceptable salts or solvates thereof.

In a preferred embodiment, the subject in need of such treatment has a disease state associated with pain, such as inflammatory pain, neuropathic pain, cancer pain, acute pain, chronic pain, surgical pain, dental pain, premenstrual pain, visceral pain, pain due to burns, migraine or cluster headaches, neuralgias, post traumatic injuries, pain associated with functional bowel disorders such as irritable bowel syndrome, hyperalgesia, or complex regional syndromes.

In another preferred embodiment, the subject in need of such treatment has a disease state associated with inflammation, such as bacterial, fungal infections, viral infections, idiopathic bladder inflammation, over-use, old age, nutritional deficiencies, prostatis, or conjunctivitis pain.

In another preferred embodiment, the subject in need of such treatment has a disease state associated with urinary tract disease state, such as bladder outlet obstruction, urinary incontinence, reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urge incontinence, urethritis, prostatitis, pelvic pain syndrome, prostatodynia, cystitis, or idiophatic bladder hypersensitivity.

In another preferred embodiment, the subject in need of such treatment has a disease state associated with respiratory disease states from allergies or asthma.

In another preferred embodiment, the subject in need of such treatment has a disease state associated with edema formation or hypotensive vascular diseases.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a," "an" and "the" include plural referents unless the context clearly dictates otherwise.

"Acyl" (or alkanoyl) means the radical —C(O)—R$^a$, wherein R$^a$ is lower alkyl as defined herein. Examples of acyl radicals include, but are not limited to, formyl, acetyl, propionyl, butyryl, and the like.

"Alkyl" means the monovalent linear or branched saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, isobutyl, sec-butyl, tert-butyl, pentyl, n-hexyl, octyl, dodecyl, and the like.

"Lower alkyl" or "(C$_{1-6}$)alkyl" means the monovalent linear or branched saturated hydrocarbon radical, consisting solely of carbon and hydrogen atoms, having from one to six carbon atoms inclusive, unless otherwise indicated. Examples of lower alkyl radicals include, but are not limited to, methyl, ethyl, propyl, isopropyl, sec-butyl, tert-butyl, n-butyl, n-pentyl, n-hexyl, and the like.

"Alkoxy" means the radical —O—R$^b$, wherein R$^b$ is a (C$_{1-6}$)alkyl radical as defined herein. Examples of alkoxy radicals include, but are not limited to, methoxy, ethoxy, isopropoxy, and the like.

"Alkoxycarbonyl" means the radical —C(O)—OR$^c$ wherein R$^c$ is a (C$_{1-6}$) alkyl radical as defined herein. Examples of alkoxycarbonyl radicals include, but are not limited to, methoxycarbonyl, ethoxycarbonyl, isopropoxycarbonyl, and the like.

"Alkylamino" means the radical —NHR$^d$, wherein R$^d$ is a (C$_{1-6}$)alkyl radical as defined herein. Examples of alkylamino radicals include, but are not limited to, methylamino, ethylamino, butylamino, and the like.

"Alkylaminocarbonyl" means the radical —C(O)—NHR$^e$ wherein R$^e$ is a (C$_{1-6}$) alkyl radical as defined herein. Examples of alkylaminocarbonyl radicals include, but are not limited to, methylaminocarbonyl, ethylaminocarbonyl, isopropylaminocarbonyl, and the like.

"Alkylsulfonyl" means the radical —SO$_2$R$^f$ wherein R$^f$ is a (C$_{1-6}$) alkyl radical as defined herein. Examples of alkylsulfonyl radicals include, but are not limited to, methanesulfonyl, ethanesulfonyl, propanesulfonyl, and the like.

"Aralkyl" means the radical —R$^g$R$^h$ wherein R$^g$ is a (C$_{1-6}$) radical as defined herein, and R$^h$ is a lower aryl radical as defined herein. Examples of aralkyl radicals include, but are not limited to, benzyl, phenylethyl, 3-phenylpropyl, and the like.

"Aralkyloxy" means the radical —O—R$^i$, wherein R$^i$ is an aralkyl radical as defined herein. Examples of aralkyloxy radicals include, but are not limited to, benzyloxy, phenylethyloxy, and the like.

"Aryl" means the monovalent monocyclic aromatic hydrocarbon radical consisting of one or more fused rings in which at least one ring is aromatic in nature, which can be optionally substituted with one or more substituents independently selected from lower alkyl, alkoxy, hydroxy, cyano, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino, methylenedioxy, ethylenedioxy, and/or optionally substituted heterocyclyl, unless otherwise indicated. Examples of aryl radicals include, but are not limited to, phenyl, naphthyl, biphenyl, indanyl, and the like.

"Aryloxy" means the radical —O—R$^j$, wherein R$^j$ is an aryl radical as defined herein. Examples of aryloxy radicals include, but are not limited to, phenoxy and the like.

"Cycloalkyl" means the monovalent saturated carbocyclic radical consisting of one or more rings, which can be optionally substituted with one or more substituents independently selected from hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or trifluoromethyl, unless otherwise indicated. Examples of cycloalkyl radicals include, but are not limited to, cyclopropyl, cyclobutyl, 3-ethylcyclobutyl, cyclopentyl, cyclopentyl, cycloheptyl, and the like.

"Dialkylamino" means the radical —NR$^k$R$^l$ wherein R$^k$ and R$^l$ are each independently (C$_{1-6}$)alkyl radicals as defined herein. Examples of dialkylamino radicals include, but are not limited to, dimethylamino, methyl ethylamino, diethylamino, methyl propylamino, and the like.

"Dialkylaminocarbonyl" means the radical —C(O)-NR$^m$R$^n$ wherein R$^m$ and R$^n$ are each independently a (C$_{1-6}$)alkyl radical as defined herein. Examples of dialkylaminocarbonyl radicals include, but are not limited to, dimethylaminocarbonyl, diethylaminocarbonyl, methyl propylaminocarbonyl, and the like.

"Ethylenedioxy" means the radical —OCH$_2$CH$_2$O—.

"Halogen" or "halo" means the radical fluoro, bromo, chloro, and/or iodo.

"Haloalkyl" means alkyl as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Heteroaryl" means the monovalent aromatic carbocyclic radical having one or more rings incorporating one, two, or three heteroatoms within the ring independently selected from nitrogen, oxygen, or sulfur. The heteroaryl radical can be optionally substituted with one or more substituents independently selected from hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or trifluoromethyl, unless otherwise indicated. Examples of heteroaryl radicals include, but are not limited to, imidazolyl, oxazolyl, pyrazinyl, thiophenyl, quinolyl, benzofuryl, pyridiyl, indolyl, pyrrolyl, pyranyl, naphtyridinyl, and the like.

"Heterocyclyl" means a monovalent saturated carbocyclic radical of 3 to 7 ring atoms, consisting of one or more rings and incorporating one, two, or three heteroatoms independently selected from nitrogen, oxygen or sulfur. The heterocyclic radical can be optionally substituted with one or more substituents independently selected from lower alkyl, alkoxy, acyl, thioalkyl, halo, hydroxy, hydroxyalkyl, cyano, haloalkyl, nitro, alkoxycarbonyl, amino, alkylamino, dialkylamino, aminocarbonyl, alkylaminocarbonyl, dialkylaminocarbonyl, alkoxycarbonyl, carbonylamino, alkylsulfonyl, aminosulfonyl, heteroaryloxy, and/or sulfonylamino, unless otherwise indicated. Examples of heterocyclyl radicals include, but are not limited to, morpholinyl, piperazinyl, methylpiperazinyl, piperidinyl, pyrrolidinyl, tetrahydropyranyl, thiomorpholinyl, and the like.

"Hydroxyalkyl" means alkyl as defined herein, substituted with one or more hydroxy groups. Examples of hydroxyalkyl radicals include, but are not limited to, hydroxymethyl, 2-hydroxyethyl, 2-hydroxypropyl, 3-hydroxypropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl, and 2-(hydroxymethyl)-3-hydroxypropyl, and the like.

"Methylenedioxy" means the radical —OCH$_2$O—.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Optionally substituted phenyl" means a phenyl ring which is optionally substituted with one or more substituents independently selected from (C$_{1-6}$)alkyl, alkoxy, hydroxy, cyano, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino, methylenedioxy, ethylenedioxy, and/or optionally substituted heterocyclyl, unless otherwise indicated.

"Isomer" means different compounds that have the same molecular formula, but differ in the nature or the sequence of bonding of their atoms or in the arrangement of their atoms in space. Isomers that differ in the arrangement of their atoms in space are termed "stereoisomers". Stereoisomers that are mirror images of each other and optically active are termed "enantiomers", and stereoisomers that are not mirror images of one another are termed "diastereoisomers".

"Atropic isomer" means the isomers owing their existence to restricted rotation caused by hindrance of rotation of large groups about a central bond.

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog (Cahn et al., *Angew. Chem. Inter*. Edit. 1966, 5, 385; errata 511; Cahn et al., *Angew. Chem.* 1966, 78, 413; Cahn and Ingold *J. Chem. Soc.* (London) 1951, 612; Cahn et al., *Experientia* 1956, 12, 81; Cahn, *J. Chem.Educ.* 1964, 41, 116).

"Geometric isomer" means the diastereomers that owe their existence to hindered rotation about double bonds. These configurations are differentiated in their names by the prefixes cis- and trans-, or Z and E, which indicate that the groups are on the same or opposite side of the double bond in the molecule according to the Cahn-Ingold-Prelog rules.

"Leaving group" means the group with the meaning conventionally associated with it in synthetic organic chemistry, i.e., an atom or group displaceable under alkylating conditions. Examples of a leaving group include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" has the meaning conventionally associated with it in synthetic organic chemistry, i.e., a group which selectively blocks one reactive site in a multifunctional compound such that a chemical reaction can be carried out selectively at another unprotective reactive site. Certain processes of this invention rely upon the protecting groups to block reactive oxygen atoms present in the reactants. Acceptable protective groups for alcoholic or phenolic hydroxyl groups, which may be removed successively and selectively, include groups protected as acetates, haloalkyl carbonates, benzyl ethers, alkylsilyl ethers, heterocyclyl ethers, methyl or other alkyl ethers, and the like. Protective or blocking groups for carboxyl groups are similar to those described for hydroxyl groups, preferably tert-butyl, benzyl, or methyl esters. Examples of protecting groups can be found in T. W. Greene et al., *Protective Groups in Organic Chemistry*, 1991, J. Wiley, $2^{nd}$ ed., and Harrison et al., *Compendium of Synthetic Organic Methods*, 1971–1996, Vols. 1–8, J. Wiley and Sons.

"Amino-protecting group" or "N-protecting group" means the protecting group that refers to those organic groups intended to protect the nitrogen atom against undesirable reactions during synthetic procedures and includes, but is not limited to, benzyl, benzyloxycarbonyl (carbobenzyloxy, CBZ), p-methoxybenzyl-oxycarbonyl, p-nitrobenzyloxycarbonyl, tert-butoxycarbonyl (BOC), trifluoroacetyl, and the like.

"Deprotection" or "deprotecting" is the process by which a protective group is removed after the selective reaction is completed. Certain protective groups may be preferred over others due to their convenience or relative ease of removal. Deprotecting reagents for protected hydroxyl or carboxyl groups include potassium or sodium carbonates, lithium hydroxyde in alcoholic solutions, zinc in methanol, acetic acid, trifluoroacetic acid, palladium catalysts, or boron tribromide, and the like.

"Inert organic solvent" or "inert solvent" means a solvent inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable carrier" means a carrier that is useful in preparing a pharmaceutical composition that is generally compatible with the other ingredients of the composition, not deleterious to the recipient, and neither biologically nor otherwise undesirable, and includes a carrier that is acceptable for veterinary use or human pharmaceutical use. "A pharmaceutically acceptable carrier" as used in the specification and claims includes both one and more than one such carrier.

"Pharmaceutically acceptable salt" of a compound means a salt that is pharmaceutically acceptable and that possesses the desired pharmacological activity of the parent compound. Such salts, for example, include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxy-ethanesulfonic acid, benzenesulfonic acid, 2-napthalenesulfonic acid, 4-methylbicyclo-[2.2.2]oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like;

(2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methyl-glucamine, and the like. Acceptable inorganic bases include aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

"Pharmacological effect" as used herein encompasses effects produced in the subject that achieve the intended purpose of a therapy. In one preferred embodiment, a pharmacological effect means the treatment of a subject in need of such treatment. For example, a pharmacological effect would be one that results in the prevention, alleviation, or reduction of a disease state associated with pain, inflammation, urinary tract disease state, or asthma in a subject in need of such treatment. In a preferred embodiment, a pharmacological effect means that the activation of the IP receptors is associated with therapeutic benefit in a subject having a disease state treatable by the administration of an IP receptor modulator, in particular an IP receptor antagonist.

"Subject" means mammals and non-mammals. Examples of mammals include, but are not limited to, any member of the Mammalia class: humans, non-human primates such as chimpanzees and other apes and monkey species; farm animals such as cattle, horses, sheep, goats, swine; domestic animals such as rabbits, dogs and cats; laboratory animals including rodents, such as rats, mice, and guinea pigs, and the like. Examples of non-mammals include, but are not limited to birds, and the like. The term does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, and disease state being treated, the severity or the disease treated, the age and relative health of the subject, the route and form of administration, the judgement of the attending medical or veterinary practitioner, and other factors.

"Treating" or "treatment" of a disease state includes:

(1) preventing the disease state, i.e., causing the clinical symptoms of the disease state not to develop in a subject that may be exposed to or predisposed to the disease state, but does not yet experience or display symptoms of the disease state, (2) inhibiting the disease state, i.e., arresting the development of the disease state or its clinical symptoms, or (3) relieving the disease state, i.e., causing temporary or permanent regression of the disease state or its clinical symptoms.

"Disease state" means any disease, disorder, condition, symptom, or indication.

"Disease state associated with the urinary tract" or "urinary tract disease state" or "uropathy" or "symptoms of the urinary tract", used interchangeably, means the pathologic changes in the urinary tract, or dysfunction of urinary bladder smooth muscle or its innervation causing disordered urinary storage or voiding. Symptoms of the urinary tract include (also known as detrusor hyperactivity), outlet obstruction, outlet insufficiency, and pelvic hypersensitivity.

"Outlet insufficiency" includes, but is not limited to, urethral hypermobility, intrinsic sphincteric deficiency, or mixed incontinence. It is usually symptomatically manifested as stress incontinence.

"Outlet obstruction" includes, but is not limited to, benign prostatic hypertrophy (BPH), urethral stricture disease, tumors, and the like. It is usually symptomatically manifested as obstructive (low flow rates, difficulty in initiating urination, and the like), and irritative (urgency, suprapubic pain, and the like).

"Overactive bladder" or "detrusor hyperactivity" includes, but is not limited to, the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

"Pelvic Hypersensitivity" includes, but is not limited to, pelvic pain, interstitial (cell) cystitis, prostadynia, prostatis, vulvadynia, urethritis, orchidalgia, and the like. It is symptomatically manifested as pain, inflammation or discomfort referred to the pelvic region, and usually includes symptoms of overactive bladder.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, $28^{th}$ Edition, W. B. Saunders Company, Philadelphia, Pa.). The goal of treatment of pain is to reduce the degree of severity of pain perceived by a treatment subject.

"Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Modulator" means a molecule such as a compound that interacts with a target. The interactions include, but are not limited to, agonist, antagonist, and the like, as defined herein.

"Agonist" means a molecule such as a compound, a drug, an enzyme activator or a hormone that enhances the activity of another molecule or receptor site.

"Antagonist" means a molecule such as a compound, a drug, an enzyme inhibitor, or a hormone, that diminishes or prevents the action of another molecule or receptor site.

Nomenclature

The naming of the compounds of this invention is illustrated below:

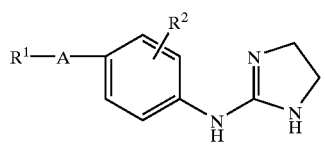

(I)

In general, the nomenclature used in this Application is generally based on AutoNom™, v.4, a Beilstein Institute computerized system for the generation of IUPAC systematic nomenclature. However, because a strict adherence to these recommendations would result in the names changing substantially when only a single substituent is changed, compounds have been named in a manner that maintains consistency of nomenclature for the basic molecule.

For example, a compound of Formula I wherein A is —CO(CH$_2$)$_2$—, R$^1$ is 4-fluorophenyl, and R$^2$ is hydrogen, is named 4-[4-(4,5-dihydro-1H-imidazol-2-yl-amino)phenyl-1-(4-fluorophenyl)propan-1-one.

For example, a compound of Formula I wherein A is —COCH$_2$O—, R$^1$ is 4-methoxyphenyl, and R$^2$ is hydrogen, is named 2-[4-(4,5-dihydro-1H-imidazol-2-ylamino)phenoxy]-1-(4-methoxyphenyl)ethanone.

As is well-known in the art, the imidazolin-2-ylamino group in compounds such as the compounds of Formula I is in tautomeric equilibrium with the imidazolin-2-ylideneamino group:

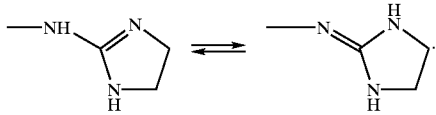

For convenience, all the compounds of Formula I are shown as having the imidazolin-2ylamino structure, but it is to be understood that compounds of both tautomeric forms are intended to be within the scope of the invention.

Preferred Compounds

Among compounds of the present invention set forth in the Summary of the Invention, certain compounds of Formula I, or individual isomers, racemic or nonracemic mixtures of isomers, or pharmaceutically acceptable salts or solvates thereof, are preferred.

A is independently in each occurrence preferably —C(O)—(CH$_2$)$_n$—.

The subscript n is independently in each occurrence preferably an integer of 2 to 4 inclusive; more preferably an integer 2.

R$^1$ is independently in each occurrence preferably aryl optionally substituted by one, two, or three substituents independently selected from lower alkyl, alkoxy, aryloxy, aralkyloxy, halogen, ethylenedioxy, or optionally substituted heterocyclyl; more preferably phenyl optionally substituted by one, two, or three substituents independently selected from halogen, alkoxy, or optionally substituted heterocyclyl; most preferably phenyl optionally substituted by one, two, or three substituents independently selected from chloro, fluoro, ethoxy, methoxy, or optionally substituted morpholin-4-yl, or optionally substituted piperazin-4-yl.

R$^2$ is independently in each occurrence preferably hydrogen.

Preferred compounds of Formula I are those, wherein A is —C(O)—(CH$_2$)$_n$— and n is 2. More preferred compounds are those wherein wherein A is —C(O)—(CH$_2$)$_n$—, n is 2, and R$^1$ is aryl optionally substituted by one, two or three substitutents independently selected from (C$_{1-6}$)-alkyl, alkoxy, aryl, aryloxy, aralkyloxy, halogen, ethylendioxy, or optionally substituted heterocyclyl.

More preferred compounds of Formula I are those wherein A is —C(O)—(CH$_2$)$_n$—, n is 2, and R$^1$ is phenyl optionally substituted with one, two or three substituents independently selected from halogen, alkoxy, or optionally substituted heterocyclyl. In a preferred embodiment R$^1$ is phenyl optionally substituted by one, two, or three substituents independently selected from halogen or alkoxy. More preferably A is —C(O)—(CH$_2$)$_n$—, n is 2, and R$^1$ is phenyl optionally substituted by one, two or three substituents independently selected from chloro, fluoro, ethoxy or methoxy; and even more preferably, A is —C(O)—(CH$_2$)$_n$—, n is 2, and R$^1$ is phenyl, 4-chlorophenyl, 2,4-dichloro-phenyl, 4-fluorophenyl, or 2-fluoro-4-methoxyphenyl.

Further preferred compounds of Formula I, are those wherein A is —C(O)—(CH$_2$)$_n$—, n is 2, and R$^1$ is phenyl substituted by one, two, or three substituents independently selected from optionally substituted heterocyclyl or halogen. Other preferred compounds are those wherein A is —C(O)—(CH$_2$)$_n$—, n is 2, and R$^1$ is phenyl substituted by one, two or three substituents independently selected from optionally substituted morpholin-4-yl, optionally substituted piperazin-4-yl, chloro, or fluoro; and even more preferred are those wherein A is —C(O)—(CH$_2$)$_n$—, n is 2, and R$^1$ is 4-morpholin-4-ylphenyl, 2-fluoro-4-morpholin-4-ylphenyl, 4-piperazin-4-yl-phenyl, 4-(ethylaminocarbonyl)-piperazin-4-ylphenyl, 4-(ethoxycarbonyl)piperazin-4-yl-phenyl, 4-(methane-sulfonyl)piperazin-4-ylphenyl, or 4-(n-propane-sulfonyl)piperazin-4-yl-phenyl.

Other preferred compounds of Formula I, are those wherein A is —C(O)—(CH$_2$)$_n$—, n is 2, and R$^1$ is aryl optionally substituted by one, two or three substituents independently selected from (C$_{1-6}$)-alkyl, alkoxy, aryloxy, aralkyloxy, halogen, ethylenedioxy, or optionally substituted heterocyclyl and R$^2$ is hydrogen.

Also preferred are compounds of Formula I, wherein A is C(O)—(CH$_2$)O—, more preferred are those wherein A is —C(O)—(CH$_2$)O— and R$^1$ is aryl optionally substituted by one, two or three substituents independently selected from (C$_{1-6}$)-alkyl, alkoxy, aryloxy, aralkyloxy, halogen, ethylenedioxy, or optionally substituted heterocyclyl. Other preferred compounds are those wherein A is —C(O)—(CH$_2$)O— and R$^1$ is phenyl optionally substituted by one, two or three substituents independently selected form alkoxy or ethylenedioxy, and even more preferred are those wherein A is —C(O)—(CH$_2$)O— and R$^1$ is phenyl optionally substituted by one, two or three substituents independently selected form alkoxy or ethylenedioxy, and R$^2$ is hydrogen.

Exemplary preferred compounds include the following compounds of Formula I, or pharmaceutically acceptable salts or solvates thereof:

(a)

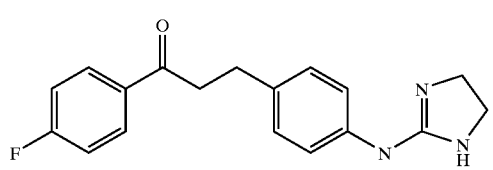

3-[4-(4,5-dihydro-1H-imidazol-2-ylamino)phenyl]-1-(4-fluorophenyl)-propan-1-one, (b)

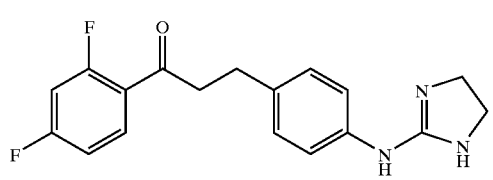

1-(2,4-difluorophenyl)-3-[4-(4,5-dihydro-1H-imidazol-2-ylamino)phenyl]-propan-1-one, (c)

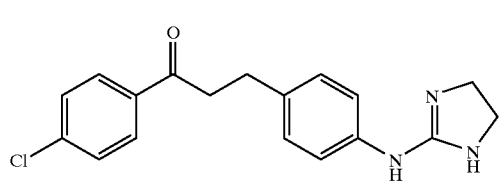

1-(4-chlorophenyl)-3-[4-(4,5-dihydro-1H-imidazol-2-ylamino)phenyl]-propan-1-one,

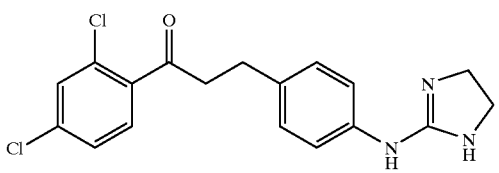

1-(2,4-dichlorophenyl)-3-[4-(4,5-dihydro-1H-imidazol-2-ylamino)phenyl]-propan-1-one,

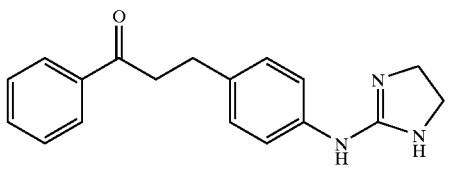

3-[4-(4,5-dihydro-1H-imidazol-2-ylamino)phenyl]-1-(phenyl)propan-1-one,

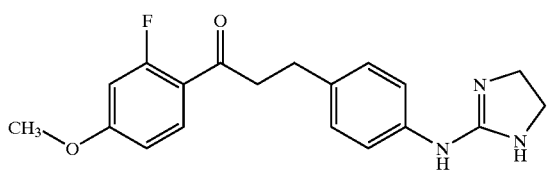

3-[4-(4,5-dihydro-1H-imidazol-2-ylamino)phenyl]-1-(2-fluoro-4-methoxy-phenyl)propan-1-one,

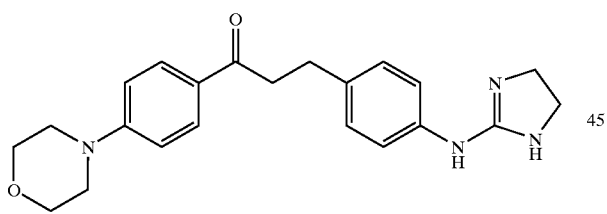

3-[4-(4,5-dihydro-1H-imidazol-2-ylamino)phenyl]-1-(4-morpholin-4-yl-phenyl)propan-1-one,

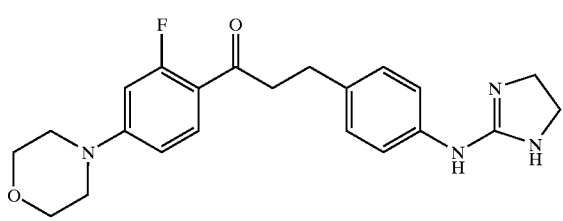

4-[4-(4,5-dihydro-1H-imidazol-2-ylamino)phenyl]-1-(2-fluoro-4-morpholin-4-ylphenyl)propan-1-one,

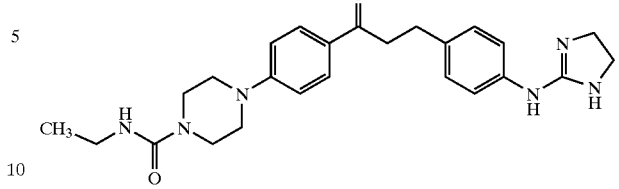

4-[4-(4,5-dihydro-1H-imidazo-2-ylamino)phenyl]-1-[4-(ethylamino-carbonyl)piperazin-4-ylphenyl]propan-1-one,

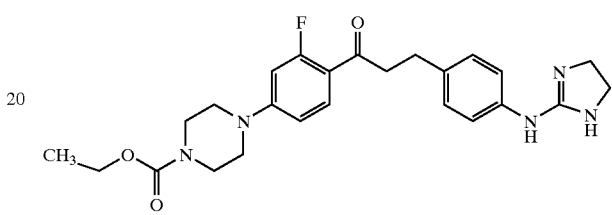

4-[4-(4,5-dihydro-1H-imidazol-2-ylamino)phenyl]-1-[4-(ethoxycarbonyl)-piperazin-4-yl-2-fluorophenyl]propan-1-one,

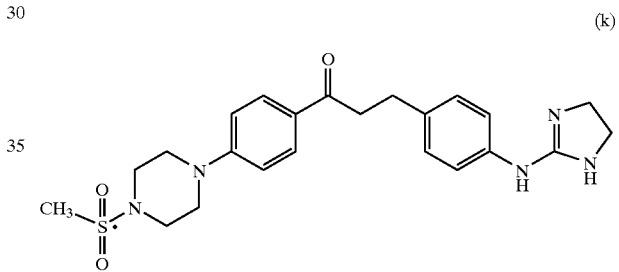

4-[4-(4,5-dihydro-1H-imidazol-2-ylamino)phenyl]-1-[4-(methanesulfonyl)-piperazin-4-ylphenyl]propan-1-one, or

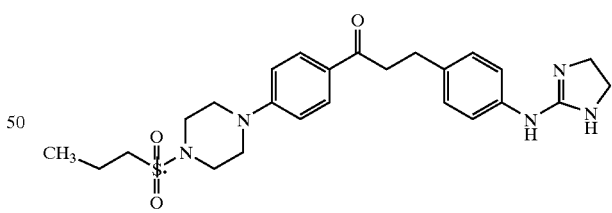

4-[4-(4,5-dihydro-1H-imidazol-2-ylamino)phenyl]-1-[4-(n-propanesulfonyl)-piperazin-4-ylphenyl]propan-1-one.

GENERAL SYNTHETIC SCHEME

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1–15; Rodd's Chemistry of Carbon Compounds, Elsevier Science Publishers, 1989, Volumes 1–5 and Supplementals; and Organic Reactions, Wiley & Sons: New York, 1991, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

Schemes A and B describe alternative methods to generate the compounds of Formula I.

Scheme A

Scheme A describes methods of preparing a compound of Formula I, in particular a compound of Formula Ia wherein A is $—CO(CH_2)_n—$, n, $R^1$, and $R^2$ are as defined in the Summary of the Invention.

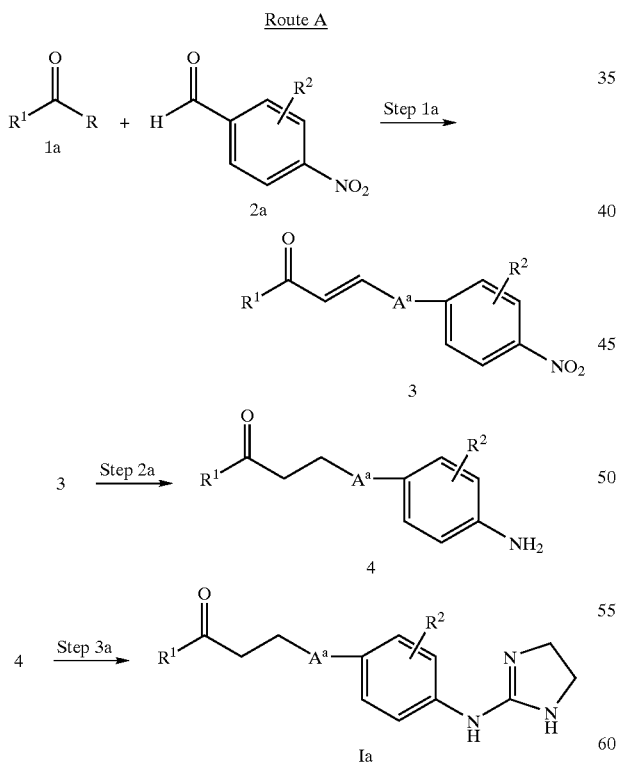

In Route A, the starting compounds, a ketone 1a (wherein R is lower alkyl) and a benzaldehyde 2a, are commercially available, for example from Aldrich Chemical Company, or are known to or can readily be synthesized by those skilled in the art.

In step 1a, reaction of a ketone 1a with a benzaldehyde 2a provides a compound of formula 3 (wherein $A^a$ is a bond or $—(CH_2)_p—$, p is an integer from 0 to 4). The reaction may be carried out by methods known in the art, for example, via a base-catalyzed aldol condensation reaction. Suitable solvents for the reaction include protic organic solvents such as methanol, ethanol, 2-methoxyethanol, and the like.

In step 2a, the selective hydrogenation the carbon-carbon double bond of and reduction of the nitro group of the compound of formula 3 to an amino group provides a compound of formula 4. Suitable reducing conditions include catalytic hydrogenation using a platinum or palladium catalyst (e.g., $PtO_2$ or palladium on carbon, preferably 10% palladium on carbon) in an inert organic solvents such as ethyl acetate, tetrahydrofuran, methanol or ethanol.

In step 3a, treatment of compound of formula 4 with a halogenated (4,5-dihydro-1H-imidazole) provides a compound of Formula Ia. The reaction proceeds on heating under reflux, typically under an inert atmosphere. Suitable solvents for the reaction include inert organic solvents such as methanol, ethanol, 2-propanol, dichloromethane, acetonitrile, or tetrahydrofuran, preferably 2-propanol. The halogenated (4,5-dihydro-1H-imidazole) is known to or can readily be synthesized by those of ordinary skill in the art, for example, synthesis of 2-chloro-4,5-dihydro-1H-imidazole is described in Trani, A. and Bellasio, E., J. Het. Chem. 1974, 11, 257.

Alternative Route A

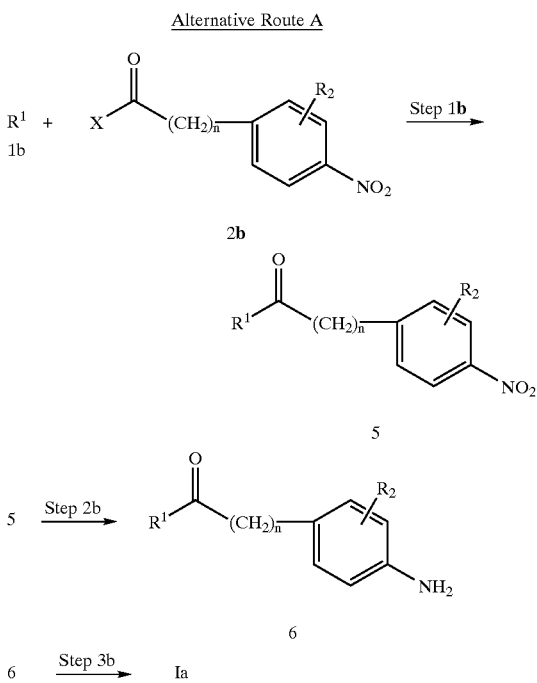

In alternative Route A, the starting compounds, an optionally substituted aryl 1b and an acyl halide 2b are commercially available, for example from Aldrich Chemical Company, or are known to or can readily be synthesized by those skilled in the art.

In step 1b, reaction of an optionally substituted aryl 1b with an acyl halide 2b wherein X is halogen, particularly chloro or bromo, provides a compound of formula 5. The reaction is carried out under conditions known to one skilled art, e.g., Friedel-Crafts reaction conditions. The reaction proceeds in the presence of a Lewis acid catalyst such as aluminum chloride in an inert organic solvent such as carbon disulfide, nitrobenzene, hexane, and the like.

In step 2b, reduction of the nitro group of compound of formula 5 to an amino group provides a compound of formula 6. The reaction may be carried out according to methods described in Scheme A, step 2a.

In step 3b, treatment of the compound of formula 6 with a halogenated (4,5-dihydro-1H-imidazole), provides a compound of Formula Ia. The reaction may be carried out according to methods described in Scheme A, step 3a.

Exemplary preparations of a compound of Formula Ia utilizing the reaction conditions described in Scheme A are described in detail in Examples 1 to 8.

Scheme B

Scheme B describes an alternative method of preparing a compound of Formula I, in particular a compound of Formula Ib wherein A is ——C(O)CH$_2$O——, and R$^1$ and R$^2$ are as defined in the Summary of the Invention.

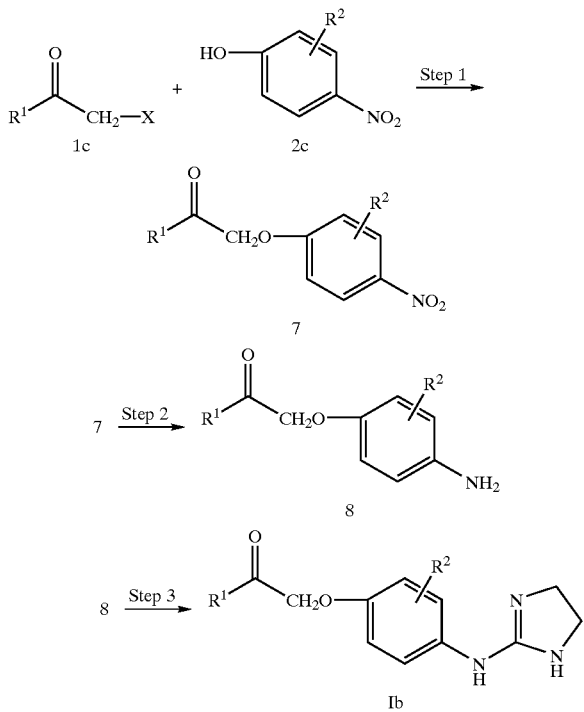

In general, the starting compounds, an alkyl halide 1c and an alcohol 2c are commercially available, for example from Aldrich Chemical Company, or are known to or can readily be synthesized by those skilled in the art.

In step 1, reaction of an alkyl halide 1c with an alcohol 2c provides a compound of formula 7. The reaction can be carried out under conditions known to one skilled in the art, e.g., Williamson synthesis reaction conditions, in the presence of a base such as potassium carbonate, sodium carbonate, or cesium carbonate. Suitable solvents for the reaction include aprotic organic solvent such as N,N-dimethylformamide, tetrahydrofuran, or dimethyl sulfoxide.

In step 2, reduction of the nitro group of compound 7 to an amino group provides a compound of formula 8. Suitable reducing conditions include catalytic hydrogenation using a platinum or palladium catalyst, or tin(II) halide, preferably tin(II) halide. Suitable solvents for the reaction include inert organic solvents such as ethyl acetate N,N-dimethylformamide, tetrahydrofuran, and the like.

In step 3, treatment of the compound of formula 6 with a halogenated (4,5-dihydro-1H-imidazole), provides a compound of Formula Ib. The reaction may be carried out according to methods described in Scheme A, step 3a.

Exemplary preparations compounds of Formula Ib utilizing the reaction conditions described in Scheme B is described in detail in Examples 9 and 10.

General Utility

The compounds of the present invention are IP receptor modulators, in particular, IP receptor antagonists, and as such possess selective antagonist activity at the IP receptor. These compounds (and compositions containing them) are expected to be useful in the prevention and treatment of a variety of diseases in mammals, especially humans.

In particular, the compounds of the invention possess anti-inflammatory and/or analgesic properties in vivo, and accordingly, are expected to find utility in the treatment of disease states associated with pain conditions from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

The compounds of the present invention are also useful in the treatment of inflammatory conditions from a variety of causes, including, but not limited to, bacterial, fungal or viral infections, rheumatoid arthritis, osteoarthritis, surgery, bladder infection or idiopathic bladder inflammation, overuse, old age, or nutritional deficiencies, prostatitis, and conjunctivitis.

The compounds of this invention are also useful in treating disease states associated with urinary tract disease states associated with bladder outlet obstruction and urinary incontinence conditions such as bladder outlet obstruction, urinary incontinence, reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urge incontinence, urethritis, prostatitis, pelvic pain syndrome, prostatodynia, cystitis, and idiophatic bladder hypersensitivity, and other symptoms related to overactive bladder.

The compounds of this invention may also find utility in the treatment of hypotensive vascular diseases such as hypotension associated with septic shock.

In addition, the compounds of this invention are useful in the treatment of respiratory diseases such as allergies and asthma.

These and other therapeutic uses are described, for example, in *Goodman & Gilman's, The Pharmacological Basis of Therapeutics*, ninth edition, McGraw-Hill, New York, 1996, Chapter 26:601–616; and Coleman, R. A., *Pharmacological Reviews*, 1994,46:205–229.

Testing

The binding affinity of these compounds to the intended target was measured with the in vitro Human Platelet IP Receptor Binding Assay as described in more detail in Example 18. Preferred compounds of Formula I have a pKi in the range of 7.1 to 9.6 in this assay.

The anti-inflammatory/analgesic activity of the compounds of this invention may be assayed by in vivo assays such as the Rat Carrageenan-Induced Mechanical Hyperalgesia Paw Assay and the Rat Complete Freund's Adjuvant-Induced Mechanical Hyperalgesia Assay, as described in more detail in Examples 19 and 20, respectively. Activity in the inhibition of bladder contractions may be assayed by in vivo assays such as the Inhibition of Bladder Contractions Induced by Isovolumetric Bladder Distension Assay and the Inhibition of Volume-induced Contracts in Rats Assay, as described in more detail in Examples 21 and 22, respectively. Activity in the inhibition of the septic shock may be assayed by in vivo assays such as the Rat Reversal of Endotoxin-Induced Hypotension Assay, as described in more detail in Example 23.

Administration and Pharmaceutical Composition

The present invention includes pharmaceutical compositions comprising at least one compound of the present invention, or individual isomers, racemic or non-racemic mixtures of isomers, or pharmaceutically acceptable salts or solvates thereof, together with at least one pharmaceutically acceptable carrier and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents.

Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 11 to 17.

The following preparations and examples are given to enable those skilled in the art to more clearly understand and to practice the present invention. They should not be considered as limiting the scope of the invention, but merely as being illustrative and representative thereof.

Efforts have been made to ensure accuracy with respect to numbers used (e.g., amounts, temperatures, etc.), but some experimental error and deviation should, of course, be allowed for as well as due to differences such as, for example, in calibration, rounding of numbers, and the like.

EXAMPLE 1

3-[4-(4,5-Dihydro-1H-imidazol-2-ylamino)phenyl]-1-(4-fluorophenyl)propan-1-one

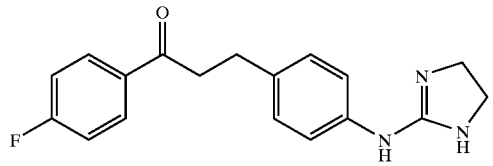

1a. 1-(4-Fluorophenyl)-3-(4-nitrophenyl)propenone

A solution of 4-fluoroacetophenone (11.05 g, 80 mmol) and 4-nitrobenzaldehyde (12.08 g, 80 mmol) in ethanol (120 mL) was cooled in an ice bath. The reaction mixture was treated with a solution of potassium hydroxide (9.86 g, 176 mmol) in water (80 mL), stirred for an additional 30 minutes, then concentrated in vacuo, and diluted with water. The resultant residue was collected by filtration and washed with water. Crystallization from ethyl acetate/hexane gave the title compound as an orange crystalline solid (16.98 g, 82.5%), m.p. 167.6–168.0° C. Analysis for $C_{15}H_{10}FNO_3$: Calcd.: C, 66.42; H, 3.72; N, 5.16. Found: C, 66.48; H, 3.65; N, 5.29.

1b. 3-(4-Aminophenyl)-1-(4-fluorophenyl)propan-1-one

A mixture of 1-(4-fluorophenyl)-3-(4-nitrophenyl)propenone (10 g, 38.9 mmol) and 10% palladium on carbon (1.0 g) in tetrahydrofuran (100 mL) and ethyl acetate (100 mL) was hydrogenated for 5 hours at ambient temperature and pressure using a hydrogen filled balloon. The catalyst was removed by filtration through a Celite pad, and the filtrate concentrated in vacuo. Purification by silica gel chromatography, eluting with ethyl acetate/hexane, gave the title compound as an oil which solidified upon standing (8.17 g, 86%), m.p. 54–55° C.

1c. 3-[4-(4,5-Dihydro-1H-imidazol-2-ylamino)phenyl]-1-(4-fluorophenyl)-propan-1-one A mixture of 3-(4-aminophenyl)-1-(4-fluorophenyl) propan-1-one (1.17 g, 4.81 mmol) and 2-chloro-4,5- dihydro-1H-imidazole sulfate (1.95 g, 9.62 mmol) (prepared according to the procedure described in Trani, A and Bellasio, E., *J. Het. Chem.* 1974, 11, 257) in 2-propanol (20 mL) was heated under reflux for 15 minutes. The reaction mixture was cooled and diluted with ethyl acetate (150 mL) and washed with 5% sodium hydroxide solution, water, and brine. The organic layer was separated and dried with potassium carbonate, and evaporated in vacuo. Purification by silica gel chromatography, eluting with 10% methanol/dichloromethane containing 1% ammonium hydroxide, gave 3-[4-(4,5-dihydro-1H-imidazol-2-ylamino)phenyl]-1-(4-fluorophenyl)propan-1-one as an oil (1.01 g, 76.5%). The oil was converted to the hydrochloride salt, m.p. 190.2–190.8° C. Analysis for $C_{18}H_{19}ClFN_3O.0.2H_2O$: Calcd.: C, 61.52; H, 5.56, N, 11.96. Found: C, 61.40; H, 5.47; N, 11.97.

EXAMPLE 2

The following compounds of Formula Ia were prepared utilizing the analogous procedures described in Example 1, but substituting 4-fluoroacetophenone in Example 1 a with corresponding compounds of formula 1a and proceeding correspondingly.

3-[4-(4,5-dihydro-1H-imidazol-2-ylamino)phenyl]-1-(4-isopropoxyphenyl)-propan-1-one hydrochloride salt, m.p. 134–137° C. Analysis for $C_{21}H_{26}ClN_3O. 0.2H_2O$: Calcd.: C, 64.42; H, 6.80; N, 10.73. Found: C, 64.49; H, 6.69; N, 10.86.

1-(2,4-difluorophenyl)-3-[4-(4,5-dihydro-1H-imidazol-2-ylamino)phenyl]-propan-1-one hydrochloride salt, m.p. 154–157° C. Analysis for $C_{18}H_{18}ClF_2N_3O. 0.2H_2O$: Calcd.: C, 58.52; H, 5.02; N, 11.37. Found: C, 58.56; H, 4.89; N, 11.47.

1-(4-chlorophenyl)-3-[4-(4,5-dihydro-1H-imidazol-2-ylamino)phenyl]-propan-1-one hydrochloride salt, m.p. 189–192° C. Analysis for $C_{18}H_{19}Cl_2N_3O$: Calcd.: C, 59.35; H, 5.26; N, 11.54. Found: C, 59.74; H, 5.33; N, 11.70.

3-[4-(4,5-dihydro-1H-imidazol-2-ylamino)phenyl]-1-(phenyl)propan-1-one hydrochloride salt, m.p. 154–155° C. Analysis for $C_{18}H_{20}ClN_3O$: Calcd.: C, 65.55; H, 6.11; N, 12.74. Found: C, 65.42; H, 6.09; N, 12.81.

3-[4-(4,5-dihydro-1H-imidazol-2-ylamino)phenyl]-1-(4-benzyloxyphenyl)-propan-1-one, m.p. 157–159° C. Analysis for $C_{25}H_{25}N_3O_2$: Calcd.: C, 75.16; H, 6.31; N, 10.52. Found: C, 74.90; H, 6.21; N, 10.62.

3-[4-(4,5-dihydro-1H-imidazol-2-ylamino)phenyl]-1-(4-phenoxyoxyphenyl)-propan-1-one oxalate salt, m.p. 176.8–178.5° C. Analysis for $C_{26}H_{25}N_3O_6$: Calcd.: C, 65.67; H, 5.30; N, 8.84. Found: C, 65.24; H, 5.22; N, 8.83.

3-[4-(4,5-dihydro-1H-imidazol-2-ylamino)phenyl]-1-(4-phenylphenyl)-propan-1-one hydrochloride salt, m.p. 157–160° C. Analysis for $C_{24}H_{24}ClN_3O.0.8H_2O$: Calcd.: C, 68.58; H, 6.14; N, 10.00. Found: C, 68.39; H, 5.92; N, 10.02.

1-(3,4-difluorophenyl)-3-[4-(4,5-dihydro-1H-imidazol-2-ylamino)phenyl]-propan-1-one hydrochloride salt, m.p. 187–189° C. Analysis for $C_{18}H_{18}ClF_2N_3O$: Calcd.: C, 59.10; H, 4.96; N, 11.490. Found: C, 58.95; H, 4.74; N, 11.54

3-[4-(4,5-dihydro-1H-imidazol-2-ylamino)phenyl]-1-(2-fluorophenyl)propan-1-one, m.p. 133–135° C. Analysis for $C_{18}H_8FN_3O$: Calcd.: C, 69.44; H, 5.83; N, 13.50. Found: C, 69.19; H, 5.77; N, 13.55.

3-[4-(4,5-dihydro-1H-imidazol-2-ylamino)phenyl]-1-(3-fluorophenyl)propan-1-one, m.p. 138–140° C. Analysis for $C_{18}H_{18}FN_3O$: Calcd.: C, 69.44; H, 5.83; N, 13.50. Found: C, 69.17; H, 5.79; N, 13.52.

1-(2,5-difluorophenyl)-3-[4-(4,5-dihydro-1H-imidazol-2-ylamino)phenyl]-propan-1-one hydrochloride salt, m.p. 193–194° C. Analysis for $C_{18}H_{18}ClF_2N_3O$: Calcd.: C, 59.10; H, 4.96; N, 11.49. Found: C, 58.87; H, 4.93; N, 11.48.

1-(3,5-difluorophenyl)-3-[4-(4,5-dihydro-1H-imidazol-2-ylamino)phenyl]-propan-1-one hydrochloride salt, m.p. 206–209° C. Analysis for $C_{18}H_{18}ClF_2N_3O.0.2H_2O$: Calcd.: C, 58.52; H, 5.02; N, 11.37. Found: C, 58.46; H, 5.16; N, 11.19.

1-(3,4-dichlorophenyl)-3-[4-(4,5-dihydro-1H-imidazol-2-ylamino)phenyl]-propan-1-one hydrochloride salt, m.p. 193–195° C. Analysis for $C_{18}H_{18}Cl_3N_3O$: Calcd.: C, 54.22; H, 4.55; N, 10.54. Found: C, 54.21; H, 4.48; N, 10.55.

3-[4-(4,5-dihydro-1H-imidazol-2-ylamino)phenyl]-1-(2-fluoro-4-methoxy-phenyl)propan-1-one hydrochloride salt, m.p. 151–153° C. Analysis for $C_{19}H_{21}ClFN_3O_2.0.5H_2O$: Calcd.: C, 58.99; H, 5.73; N, 10.86. Found: C, 58.82; H, 5.61; N, 10.96.

1-(2,4-dichlorophenyl)-3-[4-(4,5-dihydro-1H-imidazol-2-ylamino)phenyl]-propan-1-one hydrochloride salt, m.p. 173–175° C. Analysis for $C_{18}H_{18}Cl_3N_3O$: Calcd.: C, 54.22; H, 4.55; N, 10.54. Found: C, 54.65; H, 4.58; N, 10.56.

3-[4-(4,5-dihydro-1H-imidazol-2-ylamino)phenyl]-1-(6-methoxynaphthalen-2-yl)propan-1-one, m.p. 147.5–156.0° C.

3-[4-(4,5-dihydro-1H-imidazol-2-ylamino)phenyl]-1-(naphthalen-2-yl)-propan-1-one hydrochloride salt, m.p. 162.7–163.8° C. 1-(4,6-dichloro-3-fluorophenyl)-3-[4-(4,5-dihydro-1H-imidazol-2-ylamino)-phenyl]propan-1-one hydrochloride salt, m.p. 178–181° C. Analysis for $C_{18}H_{17}Cl_3FN_3O$: Calcd.: C, 51.88; H, 4.11; N, 10.08. Found: C, 51.84; H, 4.08; N, 10.16.

3-[4-(4,5-dihydro-1H-imidazol-2-ylamino)phenyl]-1-(2,3,4-trichlorophenyl)-propan-1-one hydrochloride salt, m.p. 178–179° C. Analysis for $C_{18}H_{17}Cl_4N_3O. 0.65H_2O$: Calcd.: C, 48.60; H, 4.15; N, 9.45. Found: C, 48.57; H, 3.89; N, 9.61.

3-[4-(4,5-dihydro-1H-imidazol-2-ylamino)phenyl]-1-(naphthalen-1-yl)-propan-1-one, m.p. 128.4–132.8° C.

EXAMPLE 3

3-[4-(4,5-Dihydro-1H-imidazol-2-ylamino)phenyl]-1-(4-morpholin-4-ylphenyl)-propan-1-one

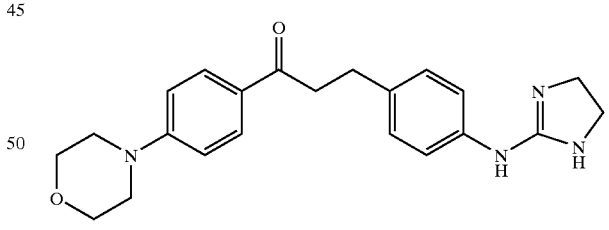

3a. 3-(4-Aminophenyl)-1-(4-morpholin-4-ylphenyl)-propan-1-one

A mixture of 3-(4-aminophenyl)-1-(4-fluorophenyl)propan-1-one (0.56 g, 2.32 mmol) (prepared as described in Example 1b) and morpholine (1.01 g, 11.62 mmol) in dimethylsulfoxide (12 mL) was heated at 100–110° C. under nitrogen for about 12 hours. The reaction mixture was cooled, diluted with ethyl acetate (150 mL), washed with cold water and brine. The organic layer was separated, dried, and evaporated in vacuo to give the title compound as an oil which was used as such in the next step.

3b. 3-[4-(4,5-Dihydro-1H-imidazol-2-ylamino)phenyl]-1-(4-morpholin-4-ylphenyl)propan-1-one Similarly following the procedures described in Example 1c, but substituting 3-(4-aminophenyl)-1-(4-fluorophenyl) propan-1-one with 3-(4-aminophenyl)-1-(4-morpholin-4-ylphenyl)propan-1-one and proceeding correspondingly, gave 3-[4-(4,5-dihydro-1H-imidazol-2-yl-amino)phenyl]-1-(4-morpholin-4-ylphenyl)-propan-1-one. m.p. 196–197.6° C. Analysis for $C_{22}H_{26}N_4O_2$: Calcd.: C, 69.82; H, 6.92; N, 14.80. Found: C, 69.46; H, 6.90; N, 14.77.

EXAMPLE 4

3-[4-(4,5-Dihydro-1H-imidazol-2-ylamino)phenyl]-1-(2-fluoro-4-morpholin-4-ylphenyl)propan-1-one

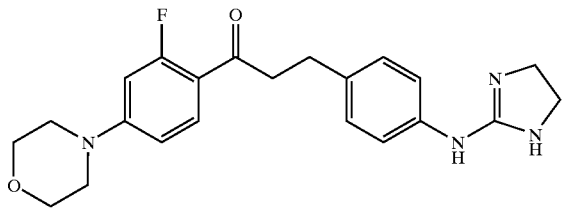

3-[4-(4,5-Dihydro-1H-imidazol-2-ylamino)phenyl]-1-(2-fluoro-4-morpholin-4-ylphenyl)propan-1-one hydrochloride salt, m.p. 168–171° C. Analysis for $C_{22}H_{26}ClFN_4O_2 \cdot 0.75H_2O$: Calcd.: C, 56.19; H, 6.21; N, 12.55. Found: C, 59.13; H, 6.00; N, 12.56, was prepared similarly to the procedures described in Example 3, but substituting 3-(4-aminophenyl)-1-(4-fluorophenyl)-propan-1-one in Example 3a with 3-(4-aminophenyl)-1-(2,4-difluorophenyl)-propan 1-one, and proceeding correspondingly.

EXAMPLE 5

3-[4-(4,5-Dihydro-1H-imidazol-2-ylamino)phenyl]-1-[4-(4-ethoxycarbonyl-piperazin-1-yl)phenyl] propan-1-one

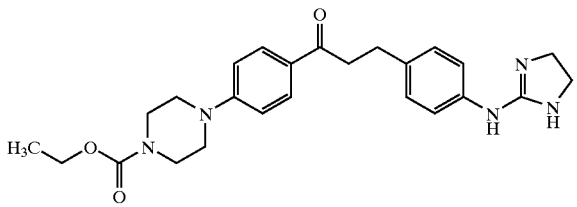

5a. 4-{4-[3-(4-Aminophenyl)propionyl]phenyl}piperazine-1-carboxylic Acid Ethyl Ester A mixture of 3-(4-aminophenyl)-1-(4-fluorophenyl) propan-1-one (1.1 g, 4.52 mmol) (prepared as described in Example 1b), 1-ethoxycarbonylpiperazine (2.15 g, 13.57 mmol), and diisopropylamine (6.5 g, 4.98 mmol) in dimethylsulfoxide (10 mL) was heated at 100–110° C. for about 12 hours. The reaction mixture was cooled, diluted with ethyl acetate (150 mL), washed with cold water and brine. The organic layer was separated, dried, and evaporated in vacua. Purification by silica gel chromatography, eluting with 60% ethyl acetate/hexane, gave the title compound, m.p. 106.3–106.7° C. Analysis for $C_{22}H_{27}N_3O_3$: Calcd.: C, 69.27; H, 7.13; N, 11.02. Found: C, 69.13; H, 7.04; N, 11.03.

5b. 3-[4-(4,5-Dihydro-1H-imidazol-2-ylamino)phenyl]-1-[4-(4-ethoxycarbonyl-piperazin-1-yl)phenyl]propan-1-one Similarly following the procedures described in Example 1c, but substituting 3-(4-aminophenyl)-1-(4-fluorophenyl) propan-1-one with 4-{4-[3-(4-aminophenyl)-propionyl] phenyl}piperazine-1-carboxylic acid ethyl ester and proceeding correspondingly gave 3-[4-(4,5-dihydro-1H-imidazol-2-ylamino)phenyl]-1-[4-(4-ethoxycarbonyl-piperazin-1-yl)phenyl]propan-1-one, m.p. 150–151.2° C. Analysis for $C_{25}H_{31}N_5O_3$: Calcd.: C, 66.79; H, 6.95; N, 15.58. Found: C, 66.42; H, 6.92; N, 15.43.

EXAMPLE 6

3-[4-(4,5-Dihydro-1H-imidazol-2-ylamino)phenyl]-1-[4-(4-methanesulfonyl-piperazin-1-yl)phenyl] propan-1-one

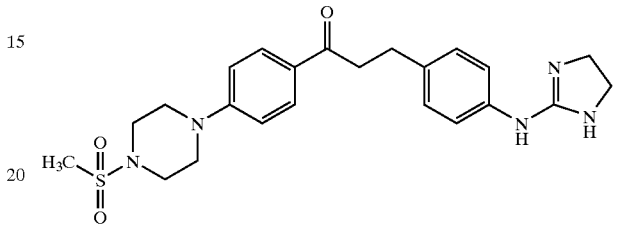

6a. 2,2,2-Trifluoro-N-{4-[3-(4-fluorophenyl)-3-oxopropyl]phenyl}-acetamide

A mixture of 3-(4-aminophenyl)-1-(4-fluorophenyl) propan-1-one (3.34 g, 13.74 mmol) (prepared as described in Example 1b), and triethylamine (4.95 g, 48.96 mmol) in dichloromethane (70 mL) was cooled in an ice bath under nitrogen. The mixture was treated with a dropwise addition of trifluoroacetic anhydride (5.14 g, 24.48 mmol). After stirring in an ice bath for 30 minutes, the mixture was quenched with methanol (30 mL) and phosphate buffer at pH 7 (30 mL), and extracted with dichloromethane. The organic layer was washed with water and brine, dried, and evaporated in vacuo. Purification by silica gel chromatography, eluting with 20% ethyl acetate/hexane, gave the title compound as a solid (0.45 g, 85%), M/S M 339. The product was used in the next step without further purification.

6b. 4-(4-{3-[4-(2,2,2-Trifluoroacetylamino)phenyl] propionyl}phenyl)piperazine-1-carboxylic Acid Tert-butyl Ester Similarly following the procedure described in Example 5, but substituting 3-(4-amino-phenyl)-1-(4-fluorophenyl) propan-1-one with 2,2,2-trifluoro-N-{4-[3-(4-fluorophenyl)-3-oxopropyl]phenyl}acetamide, and 1-ethoxycarbonylpiperazine with 1-tert-butoxycarbonylpiperazine in Example 5a, gave the title compound as a beige colored solid (64%). The product was used in the next step without further purification.

6c. 2,2,2-Trifluoro-N-{4-[3-oxo-3-(4-piperazin-1-ylphenyl)propyl]phenyl}-acetamide A suspension of 4-(4-{3-[4-(2,2,2-trifluoroacetylamino) phenyl]propionyl}-phenyl)piperazine-1-carboxylic acid tert-butyl ester (2.5 g, 4.95 mmol) in dichloromethane (10 mL) and trifluoroacetic acid (10 mL) was stirred at room temperature for 1 hour. The reaction mixture was concentrated in vacuo and diluted with water. The resultant white solid was collected, washed with water, dried in vacuo to give the title compound (1.93 g, 96%). The product was used in the next step without further purification.

6d. 2,2,2-Trifluoro-N-(4-{3-[4-(4-methanesulfonylpiperazin-1-yl)-phenyl]-3-oxopropyl}phenyl)acetamide A solution of 2,2,2-trifluoro-N-{4-[3-oxo-3-(4-piperazin-1-ylphenyl)propyl]-phenyl}acetamide (0.45 g, 1.1 mmol) was treated with methanesulfonyl chloride (0.15 g, 1.32 mmol) and triethylamine (0.28 g, 2.75 mmol) in N,N-dimethyl-formamide (5 mL). The reaction mixture was stirred for 15 minutes at 0° C., diluted with ice water, and extracted with ethyl acetate. The organic extract was washed with water and brine, dried, and concentrated in vacuo to give the title compound as a white solid (0.45 g, 85%).

6e. 3-(4-Aminophenyl)-1-[4-(4-methanesulfonylpiperazin-1-yl)-phenyl]-propan-1-one A mixture of 2,2,2-trifluoro-N-(4-{3-[4-(4-methanesulfonylpiperazin-1-yl)-phenyl]-3-oxopropyl}phenyl)acetamide (0.43 g, 0.88 mmol), and a solution of potassium carbonate (0.61 g, 4.39 mmol) in water (10 mL), and methanol (20 mL) was warmed on a steam bath, then stirred at room temperature for about 12 hours. The reaction mixture was concentrated to one-third volume, diluted with cold water, and extracted with dichloromethane. The organic extract was washed with water, brine, dried, and concentrated in vacuo. Purification by silica gel chromatography, eluting with 2% methanol in dichloromethane gave the title compound as a white solid (0.28 g, 82%), m. p.166.5–170.0° C.

6f. 3-[4-(4,5-Dihydro-1H-imidazol-2-ylamino)phenyl]-1-[4-(4-methanesulfonyl-piperazin-1-yl)phenyl]propan-1-one Similarly, following the procedures described in Example 1c, but substituting 3-(4-amino-phenyl)-1-(4-fluorophenyl) propan-1-one with 3-(4-aminophenyl)-1-[4-(4-methanesulfonylpiperazin-1-yl)-phenyl]propan-1-one and proceeding correspondingly, gave 3-[4-(4,5-dihydro-1H-imidazol-2-ylamino)-phenyl]-1-[4-(4-methanesulfonyl-piperazin-1-yl)phenyl]-propan-1-one hydrochloride salt, m.p. 160–163° C. Analysis for $C_{23}H_{30}ClN_5O_3S \cdot 0.85H_2O$: Calcd.: C, 54.45; H, 6.30; N, 13.80. Found: C, 54.49; H, 6.01; N, 13.80.

EXAMPLE 7

The following compounds of Formula Ia wherein $R^1$ is substituted piperazin-4-ylphenyl, were prepared utilizing the analogous procedures described in Examples 5 or 6, but substituting 1-ethoxycarbonylpiperazine with other piperazinyl derivatives or methanesulfonyl chloride with other halides, respectively.

3-[4-(4,5-dihydro-1H-imidazol-2-ylamino)phenyl]-1-[4-(4-methylpiperazin-1-yl)phenyl]propan-1-one, m.p. 176–178° C. Analysis for $C_{23}H_{29}N_5O$: Calcd.: C, 70.56; H, 7.47; N, 17.89. Found: C, 70.29; H, 7.38; N, 17.80.

1-[4-(4-acetylpiperazin-1-yl)phenyl]-3-[4-(4,5-dihydro-1H-imidazol-2-ylamino)phenyl]propan-1-one, m.p. 228–230° C. Analysis for $C_{24}H_{29}N_5O_2$: Calcd.: C, 68.71; H, 6.97; N, 16.69. Found: C, 68.33; H, 6.98; N, 16.50.

3-[4-(4,5-dihydro-1H-imidazol-2-ylamino)phenyl]-1-[2-(4-ethoxycarbonyl-piperazin-1-yl)-4-fluorophenyl]propan-1-one hydrochloride salt, hygroscopic foam. Analysis for $C_{25}H_{31}ClFN_5O_3 \cdot 0.25H_2O$: Calcd.: C, 58.84; H, 6.26; N, 13.72. Found: C, 58.89; H, 6.26; N, 13.63.

3-[4-(4,5-dihydro-1H-imidazol-2-ylamino)phenyl]-1-[4-(4-furan-2-yloxy-carbonylpiperazin-1-yl)phenyl]propan-1-one, m.p. 181–184° C. Analysis for $C_{27}H_{29}N_5O_3 \cdot 0.25H_2O$: Calcd.: C, 68.12; H, 6.25; N, 14.71. Found: C, 68.10; H, 6.18; N, 14.69.

3-[4-(4,5-dihydro-1H-imidazol-2-ylamino)phenyl]-1-[4-(4-propanesulfonyl-piperazin-1-yl)phenyl]propan-1-one, m.p. 200–204° C. Analysis for $C_{25}H_{33}N_5O_3S \cdot 0.4H_2O$: Calcd.: C, 61.18; H, 6.94; N, 14.27. Found: C, 61.10; H, 6.71; N, 14.08.

3-[4-(4,5-dihydro-1H-imidazol-2-ylamino)phenyl]-1-[4-(4-ethylamino-carbonylpiperazin-1-yl)phenyl]propan-1-one, foam. Analysis for $C_{25}H_{32}N_6O_2 \cdot 0.3H_2O$: Calcd.: C, 66.14; H, 7.22; N, 18.59. Found: C, 66.13; H N, 18.34.

3-[4-(4,5-dihydro-1H-imidazol-2-ylamino)phenyl]-1-[4-(4-ethoxycarbonyl-piperazin-1-yl)-2-fluorophenyl]propan-1-one hydrochloride salt, m.p. 213.5–214.3° C. Analysis for $C_{25}H_{31}ClFN_5O_3 \cdot 0.55H_2O$: Calcd.: C, 58.43; H, 6.30; N, 13.63. Found: C, 58.44; H, 6.17; N, 13.49.

3-[4-(4,5-dihydro-1H-imidazol-2-ylamino)phenyl]-1-[4-(4-propoxycarbonyl-piperazin-1-yl)phenyl]propan-1-one, m.p. 137–139° C. Analysis for $C_{26}H_{33}N_5O_3$: Calcd.: C, 67.36; H, 7.18; N, 15.11. Found: C, 67.22; H, 7.13; N, 15.11.

EXAMPLE 8

4-[4-(4,5-Dihydro-1H-imidazol-2-ylamino)phenyl]-1-(4-fluorophenyl)butan-1-one

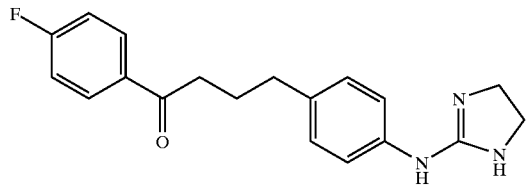

8a. 1-(4-Fluorophenyl)-4-(4-nitrophenyl)-butan-1-one

A solution of 4-(4-nitrophenyl)butyryl chloride (5.4 g, 23.7 mmol) and 4-fluorobenzene (2.6 mL, 26.2 mmol) dissolved in carbon disulfide (25 mL) was treated in portions with aluminum chloride (4.1 g, 30.75 mmol) under a nitrogen atmosphere. After the addition was complete, the reaction mixture was heated to 60–70° C. for about 12 hours. The resulting mixture was cooled in an ice bath, treated with concentrated hydrochloric acid (12 mL), and stirred for 30 minutes. The mixture was diluted with water and extracted with ethyl acetate. The organic layer was separated, washed with 1 N aqueous sodium hydroxide, water, and brine, dried and evaporated in vacuo. Purification by silica gel chromatography, eluting with 5% ethyl acetate/hexane gave the title compound as a white solid (3.81 g, 56%). The product was used in the next step.

8b. 4-(4-Aminophenyl)-1-(4-fluorophenyl)butan-1-one

A mixture of 1-(4-fluorophenyl)-4-(4-nitrophenyl)butan-1-one (0.5 g, 1.7 mmol) and 10% palladium on carbon (0.06 g) in ethyl acetate (15 mL) and tetrahydrofuran (5 mL) was hydrogenated at room temperature using the hydrogen balloon. The catalyst was removed by filtration, and the filtrate concentrated in vacuo. Purification by silica gel chromatography, eluting with 10% ethyl acetate/hexane gave the title compound as a white solid (0.34 g, 78%). The product was used in the next step.

8c. 4-[4-(4,5-Dihydro-1H-imidazol-2-ylamino)phenyl]-1-(4-fluoro-phenyl)butan-1-one Similarly following the procedures described in Example 1c, but substituting 3-(4-aminophenyl)-1-(4-fluorophenyl) propan-1-one with 4-(4-aminophenyl)-1-(4-fluorophenyl) butan-1-one and proceeding correspondingly, gave 4-[4-(4,5-dihydro-1H-imidazol-2-ylamino)phenyl]-1-(4-fluorophenyl)butan-1-one hydrochloride salt, m.p. 171–173° C. Analysis for $C_{19}H_{20}ClFN_3O$: Calcd.: C,63.07; H, 5.85; N, 11.61. Found: C, 63.21; H, 5.89; N, 11.72.

EXAMPLE 9

1-(2,3-Dihydrobenzo[1,4]dioxin-6-yl)-2-[4-(4,5-dihydro-1H-imidazol-2-ylamino)-phenoxy]ethanone

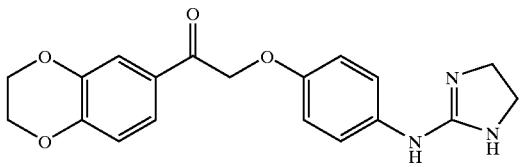

9a. 1-(2,3-Dihydrobenzo[1,4]dioxin-6-yl)-2-(4-nitrophenoxy)ethanone

A mixture of 2-bromo-1-(2,3-dihydrobenzo[1,4]dioxin-6-yl)ethanone (1.03 g, 4.00 mmol), 4-nitrophenol (0.57 g, 4.00 mmol), and cesium carbonate (1.63 g, 5.00 mmol) in dry N,N-dimethylformamide (10 mL) was stirred at room temperature for 1 hour. The reaction mixture was diluted with cold water. The resultant solid was collected by filtration gave the title compound (1.19 g, 94%). The product was used in the next step without purification.

9b. 1-(4-Aminophenoxy)-1-(2,3-dihydrobenzo[1,4]dioxin-6-yl)ethanone

A mixture of 1-(2,3-dihydrobenzo[1,4]dioxin-6-yl)-2-(4-nitrophenoxy)-ethanone (0.63 g, 2.0 mmol) and stannous chloride dihydrate (2.25 g, 10 mmol) was stirred at room temperature for 3 days. The reaction mixture was basified to pH 12 with 1N sodium hydroxide solution, and treated with methanol (75 mL) and Celite. The resulting mixture was filtered, and the filtrate evaporated in vacuo. The residue was washed with water and brine and extracted with ethyl acetate. The organic extract was washed with water and brine, dried, and removal of the solvent gave the title compound as a brown oil (0.70 g, 25%). The product was used in the next step without purification.

9c. 1-(2,3-Dihydrobenzo[1,4]dioxin-6-yl)-2-[4-(4,5-dihydro-1H-imidazol-2-yl-amino)phenoxy]ethanone Similarly following the procedures described in Example 1c, but substituting with 1-(4-aminophenoxy)-1-(2,3-dihydrobenzo[1,4]dioxin-6-yl)-ethanone and proceedingly correspondingly gave 1-(2,3-dihydrobenzo[1,4]dioxin-6-yl)-2-[4-(4,5-dihydro-1H-imidazol-2-ylamino)phenoxy]ethanone hydrochloride salt, m.p. 108–172° C. MS 354(M+1). Analysis for $C_{19}H_{20}ClN_3O_4 \cdot 0.6H_2O$: Calc C, 56.45; H, 5.38; N, 10.44. Found: C, 56.86; H, 5.09; N, 9.96.

EXAMPLE 10

2-[4-(4,5-Dihydro-1H-imidazol-2-ylamino)phenoxy]-1-(4-methoxyphenyl)ethanone

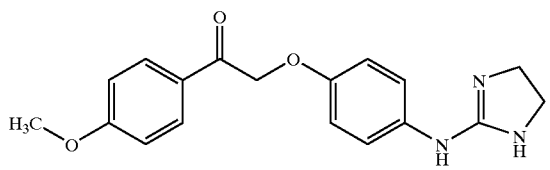

2-[4-(4,5-Dihydro-1H-imidazol-2-ylamino)phenoxy]-1-(4-methoxyphenyl)-ethanone, m.p. 65.5–69.0° C., Analysis for $C_{18}H_{20}ClN_3O_3 \cdot 0.7H_2O$: Calcd.: C, 57.74; H, 5.76; N, 11.22. Found: C, 57.69; H, 5.40; N, 10.93, was prepared similarly following the procedures described in Example 9, but substituting 2-bromo-1-(2,3-dihydrobenzo[1,4]dioxin-6-yl)ethanone in Example 9a with 2-bromo-1-phenylethanone and proceeding correspondingly.

EXAMPLE 11

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing 100 mg each; one capsule would approximate a total daily dosage.

EXAMPLE 12

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

EXAMPLE 13

Composition for Oral Administration

| Ingredient | Amount |     |
| --- | --- | --- |
| Active compound | 1.0 | g |
| Fumaric acid | 0.5 | g |
| Sodium chloride | 2.0 | g |
| Methyl paraben | 0.15 | g |
| Propyl paraben | 0.05 | g |
| Granulated sugar | 25.5 | g |
| Sorbitol (70% solution) | 12.85 | g |
| Veegum K (Vanderbilt Co.) | 1.0 | g |
| Flavoring | 0.035 | ml |
| Colorings | 0.5 | mg |
| Distilled water | q.s. to 100 | ml |

The ingredients are mixed to form a suspension for oral administration.

EXAMPLE 14

Parenteral Formulation (IV)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

EXAMPLE 15

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 16

Topical Formulation

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

EXAMPLE 17

Nasal Spray Formulations

Several aqueous suspensions containing from 0.025–0.5 percent active compound are prepared as nasal spray formulations. The formulations optionally contain inactive ingredients such as microcrystalline cellulose, sodium carboxymethylcellulose, dextrose, and the like. Hydrochloric acid may be added to adjust pH. The nasal spray formulations may be delivered via a nasal spray metered pump typically delivering 50–100 microliters of formulation per actuation. A typical dosing schedule is 2–4 sprays every 4–12 hours.

EXAMPLE 18

In vitro Human Platelet IP Receptor Radioligand Binding Assay

The in vitro Human Platelet IP Receptor Binding Assay measured the strength of a potential drug's binding affinity to its intended target.

For each drug tested, the concentration producing 50% inhibition of binding ($IC_{50}$) and Hill slope was determined using iterative curve fitting techniques. If a radioligand Kd was known the inhibition dissociation constant (Ki) of each drug was determined according to the method of Cheng & Prusoff (1973). For this receptor, a typical Kd using the preceding experimental conditions was 1 E-8 M. Usually the negative logarithm of the Ki ($pK_i$) was presented.

EXPERIMENTAL DESIGN

The following buffers were prepared using the purest available water.

| | |
| --- | --- |
| Lysis Buffer: 10 mM Tris-HCl, 1.0 mM EDTA (di-Na) | pH 7.5 @ 4° C. |
| Assay Buffer: 20 mM Tris-HCl, 5.0 mM $MgCl_2$ | pH 7.4 @ 25° C. |
| Wash Buffer: 20 mM Tris-HCl, 5.0 mM $MgCl_2$ | pH 7.4 @ 4° C. |

1. Membrane Preparation 250 mL Platelet Rich Plasma was transferred into 250 mL centrifuge tubes and spun at 6000 g for 10 min. at 20° C. Pellets were then resuspended in IP lysis buffer and homogenized using a polytron(setting 7, 1×20 sec. burst), brought up to a final volume of 180 mL and centrifuged at 40,000 g for 15 min. at 4° C. The pellets were then resuspended in IP assay buffer, protein density determined by BCA method (Pierce) and stored in 2.0 mL vials at −80° C. for subsequent assay use.

To obtain at least 80% specific binding, 50 μg protein/assay tube was used in a competition experiment. The final radioligand concentration was 1 to 3E-8 M.

2. Competition Assay

The membranes were thawed at room temperature and then diluted in assay buffer to the appropriate concentration.

First buffer, drug, radioligand, and lastly, membranes were added to the assay tubes.

The assay tubes were incubated at 25° C. for 60 min.

The assay tubes were filtered onto 0.3% PEI pre-treated glass fiber filtermats (GF/B) using Packard Top Count 96 well cell harvester. The tubes were rinsed three times with ice cold 20 mM Tris-HCl, 5 mM $MgCl_2$, pH=7.4 (3×0.5 mL/sample).

Bound radioactivity was determined using liquid scintillation counting.

Compounds of this invention were active in this assay.

EXAMPLE 19

Carrageenan-lnduced Mechanical Hyperalgesia Assay

The anti-inflammatory/analgesic activity of compounds of this invention was determined by the Carrageenan-Induced Mechanical Hyperalgesia Assay by measuring the inhibition of carrageenan-induced paw hyperalgesia in the rat, using a modification of the method described in L. O. Randall and J. J. Selitto, *Archives of International Pharmacodynamics*, 1957, 11, 409–419, and Vinegar et al., *Journal of Pharmacology and Experimental Therapeutics*, 1969, 166, 96–103.

Male Sprague-Dawley rats (130–150 g) were weighed and randomly assigned to treatment groups (n=10). To induce mechanical hyperalgesia, rats were lightly anesthetized with halothane and administered 1% carrageenan or vehicle 1 (100 μl) in the plantar surface of the left hindpaw. Rats were administered vehicle (10 ml/kg, p.o. or 1 ml/kg, i.v) or compounds of this invention (at 1, 3, 10, 30 and 100 mg/kg, p.o.) or (0.3, 1.0, 3.0 and 10 mg/kg, i.v.) one hour before testing. Mechanical hyperalgesia was measured using an Analgesy-meter (UGO BASILE, Biological Research Apparatus, Comerio, Italy). The vehicle- or carrageenan-treated hindpaw was placed on the dome of the apparatus, plantar surface facing down. A constantly increasing force was then applied to the dorsal surface of the paw. The force at which the rat withdrew its paw, struggled, or vocalized was considered the end point.

Treatment groups were compared using a one-way analysis of variance on the paw withdrawal force (RESP). Pairwise comparisons for the drug-treated groups to the vehicle group were made using Fisher's LSD strategy and Dunn's procedure. Percent inhibition of mechanical hyperalgesia was calculated for each animal, and the average $ID_{50}$ value was estimated using the following sigmoidal model:

% inhibition=$100/(1+\exp((ID_{50}-\text{dose})/N))$ where $ID_{50}$ is the dose of the compound needed to inhibit half of the maximum response (i.e., 100% in this model) and N is a curvature parameter.

The compounds of this invention were active in this assay.

EXAMPLE 20

Complete Freund's Adjuvant-induced Mechanical Hyperalgesia Assay

The anti-inflammatory/analgesic activity of compounds of this invention may also be determined using an adjuvant-induced arthritis pain model in the rat, where pain is assessed by the animal's response to the squeezing of the inflamed foot, using a modification of the method described in J. Hylden et al., *Pain* 1989, 37, 229–243. The modification includes the assessment of hyperalgesia instead of changes in activity of spinal cord neurons.

Briefly, rats were weighed and randomly assigned to treatment groups. To induce mechanical hyperalgesia, rats were lightly anesthetized with halothane and 100 μl of Complete Freund's Adjuvant or saline was administered into the plantar surface of the left hindpaw. Twenty-four hours later, water (vehicle) or compounds of this invention were orally administered to the rats one hour before testing. Mechanical hyperalgesia was measured using an Analgesy-meter (UGO BASILE, Biological Research Apparatus, Comerio, Italy). The saline or carrageenan-treated hindpaw was placed on the dome of the apparatus, plantar surface facing down. A constantly increasing force was then applied to the dorsal surface of the paw, and the force at which the rat withdrew its paw, struggled, or vocalized was considered the end point. The treatment groups were compared using a one-way analysis of variance on the paw withdrawal force. Percent inhibition was calculated for each animal in the form:

$100 \times ((c/d-c/v)+(s/v-c/v))$ where c/d is the paw withdrawal force for the carrageenan-treated paw in an animal to which drug has been administered; c/v is the paw withdrawal force for the carrageenan-treated paw in an animal to which vehicle has been administered; and s/v is the paw withdrawal force for the saline-treated paw in an animal to which vehicle has been administered. Significance was determined using Student's t-test.

The compounds of the invention were active in this assay.

EXAMPLE 21

Inhibition of Bladder Contractions Induced by Isovolumetric Bladder Distension in Rats The inhibition of bladder contractions was determined by an assay using a modification of the method described in C. A. Maggi et al., *J. Pharm. and Exper. Therapeutics*, 1984, 230, 500–513.

Briefly, male Sprague-Dawley rats (200–250 g) were weighed and randomly assigned to treatment groups. A catheter was inserted through the urethra into the bladder to induce bladder contractions, and a warm saline solution (5 mL) was infused. Rhythmic contractions were produced in about 30% of the animals. The compounds of the invention (0.1, 0.3 or 1 mg/kg) were administered intravenous at the onset of regular rhythmic contractions. The effects on rhythmic contracts were then measured.

The compounds of this invention were active in this assay.

EXAMPLE 22

Inhibition of Volume-induced Contractions in Rats

The inhibition of bladder contractions was determined by an assay using a modification of the method described in S. S. Hegde et al., *Proceedings of the 26th Annual Meeting of the International Continence Society* (Aug. 27th–30th) 1996, Abstract 126.

Female Sprague-Dawley rats were anesthetized with urethane and instrumented for intravenous administration of drugs and, in some cases, measurement of arterial pressure, heart rate and intra-bladder pressure. The effect of test compounds on volume-induced bladder contractions was determined in separate groups of animals. Volume-induced reflex bladder contractions were induced by filling the bladder with saline. The test compounds were administered intravenously in a cumulative manner at 10-minute intervals. Atropine (0.3 mg/kg, iv) was administered at the end of the study as a postive control.

The compounds of this invention were active in this assay.

EXAMPLE 23

Reversal of Endotoxin-Induced Hypotension in Rats

Septic shock, sometimes referred to as endotoxic shock, is caused by the presence of infectious agents, particularly bacterial endotoxins, in the bloodstream and is characterized by hypotension and organ dysfunction. Many symptoms of septic shock, in particular, hypotension, are induced in the rat by the administration of bacterial endotoxins. The ability of a compound to inhibit endotoxin-induced hypotension is therefore predictive of the utility of the compound in the treatment of septic or endotoxic shock.

The activity of the compounds of the invention in the treatment of septic or endotoxic shock was determined by measuring the reversal of endotoxin-induced hypotension in the rat, using a modification of the method described in M. Giral et al., *British Journal of Pharmacology*, 1969, 118, 1223–1231.

Briefly, adult rats (>200 g) were anesthetized with an inhalation anesthetic and femoral arteries and veins were cannulated for insertion of blood pressure transducers and drug administration lines, respectively. They were placed in Mayo restrainers while still under the influence of the anesthetic. After recovery from anesthesia and stabilization of heart rate and blood pressure (which typically required about 30 minutes), endotoxin (50 mg/kg *E. coli* and 25 mg/kg Salmonella) was administered intravenously. Changes in blood pressure and heart rate were monitored. After one hour, compounds of this invention or vehicle were also administered intravenously, and cardiovascular parameters were continuously monitored for the next three hours. Responses are represented as percentage return to initial diastolic blood pressure. Significance was determined using Student's t-test.

The compounds of this invention were active in this assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound comprising Formula I:

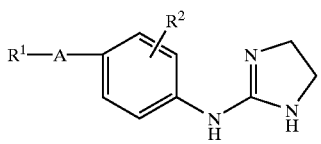

(I)

wherein:
$R^1$ is an optionally substituted aryl; wherein $R^1$ is optionally substituted by one, two, or three substituents independently selected from $(C_{1-6})$-alkyl, alkoxy, aryloxy, aralkyloxy, halogen, haloalkyl, hydroxy, hydroxyalkyl, nitro, cycloalkyl, amino, alkylamino, dialkylamino, methylenedioxy, ethylenedioxy, and optionally substituted heterocyclyl;
$R^2$ is hydrogen, $(C_{1-6})$-alkyl, or halogen;
A is —C(O)—(CH$_2$)$_n$— or —C(O)CH$_2$O—; and
the subscript n is an integer from 2 to 6 inclusive; or an individual isomer, racemic or non-racemic mixture of isomers, or a
pharmaceutically acceptable salt or solvate thereof.

2. The compound of claim 1 wherein A is —C(O)—(CH$_2$)$_n$— and n is an integer of 2.

3. The compound of claim 2 wherein $R^1$ is aryl optionally substituted by one, two, or three substituents independently selected from $(C_{1-6})$alkyl, alkoxy, aryloxy, aralkyloxy, halogen, ethylenedioxy, and optionally substituted heterocyclyl.

4. The compound of claim 3 wherein $R^1$ is phenyl optionally substituted by one, two, or three substituents independently selected from halogen, alkoxy, and optionally substituted heterocyclyl.

5. The compound of claim 4 wherein $R^1$ is phenyl optionally substituted by one, two, or three substituents independently selected from halogen and alkoxy.

6. The compound of claim 5 wherein $R^1$ is phenyl optionally substituted by one, two, or three substituents independently selected from chloro, fluoro, ethoxy, and methoxy.

7. The compound of claim 6 wherein $R^1$ is phenyl, 4-chlorophenyl, 2,4-dichloro-phenyl, 4-fluorophenyl, 2,4-difluorophenyl, or 2-fluoro-4-methoxyphenyl.

8. The compound of claim 3 wherein $R^1$ is phenyl substituted by one, two, or three substituents independently selected from optionally substituted heterocyclyl and halogen.

9. The compound of claim 8 wherein $R^1$ is phenyl substituted by one, two, or three substituents independently selected from optionally substituted morpholin-4-yl, optionally substituted piperazin-4-yl, chloro, and fluoro.

10. The compound of claim 9 wherein $R^1$ is 4-morpholin-4-ylphenyl, 2-fluoro-4-morpholin-4-ylphenyl, 4-piperazin-4-ylphenyl, 4-(ethylaminocarbonyl)-piperazin-4-ylphenyl, 4-(ethoxycarbonyl)piperazin-4-ylphenyl, 4-(methanesulfonyl)piperazin-4-ylphenyl, or 4-(n-propane-sulfonyl)piperazin-4-yl-phenyl.

11. The compound of claim 3 wherein $R^2$ is hydrogen.

12. The compound of claim 1 wherein A is —C(O)—(CH$_2$)$_n$—, n is an integer of 2, $R^1$ is 4-fluorophenyl, and $R^2$ is hydrogen.

13. The compound of claim 1 wherein A is —C(O)CH$_2$O—.

14. The compound of claim 13 wherein $R^1$ is aryl optionally substituted by one, two, or three substituents independently selected from $(C_{1-6})$-alkyl, alkoxy, aryloxy, aralkyloxy, halogen, ethylenedioxy, and optionally substituted heterocyclyl.

15. The compound of claim 14 wherein $R^1$ is phenyl optionally substituted by one, two, or three substituents independently selected from alkoxy and ethylenedioxy.

16. The compound of claim 15 wherein $R^2$ is hydrogen.

17. The compound of claim 1, or an individual isomer, racemic or non-racemic mixture of isomers, or pharmaceutically acceptable salt or solvate thereof, which is:

4-[4-(4,5-d ihydro-1H-imidazol-2-ylamino)phenyl]-1-(4-fluoro-phenyl)propan-1-one, 1-(2,4-difluorophenyl)-4-[4-(4,5-dihydro-1H-imidazol-2-yl-amino)phenyl]propan-1-one, 1-(4-chlorophenyl)-4-[4-(4,5-dihydro-1H-imidazol-2-yl-amino)phenyl]propan-1-one, 1-(2,4-dichlorophenyl)-4-[4-(4,5-dihydro-1H-imidazol-2-yl-amino)phenyl]propan-1-one, 4-[4-(4,5-dihydro-1H-imidazol-2-ylamino)phenyl]-1-(phenyl)propan-1-one, 4-[4-(4,5-dihydro-1H-imidazol-2-ylamino)phenyl]-1-(2-fluoro-4-methoxyphenyl)propan-1-one, 4-[4-(4,5-dihydro-1H-imidazol-2-ylamino)phenyl]-1-(4-morpholin-4-ylphenyl)propan-1-one, 4-[4-(4,5-dihydro-1H-imidazol-2-ylamino)phenyl]-1-(2-fluoro-4-morpholin-4-ylphenyl)propan-1-one, 4-[4-(4,5-dihydro-1H-imidazol-2-ylamino)phenyl]-1-[4-(ethylamino-carbonyl)piperazin-4-ylphenyl]propan-1-one, 4-[4-(4,5-dihydro-1H-imidazol-2-ylamino)phenyl]-1-[4-(ethoxy-carbonyl)piperazin-4-yl-2-fluorophenyl]propan-1-one, 4-[4-(4,5-dihydro-1H-imidazol-2-ylamino)phenyl]-1-[4-(methane-sulfonyl)piperazin-4-ylphenyl]propan-1-one, or 4-[4-(4,5-dihydro-1H-imidazol-2-ylamino)phenyl]-1-[4-(n-propane-sulfonyl)piperazin-4-ylphenyl]propan-1-one.

18. The compound of claim 1, or an individual isomer, racemic or non-racemic mixture of isomers, or pharmaceutically acceptable salt or solvate thereof, which is:

(a)

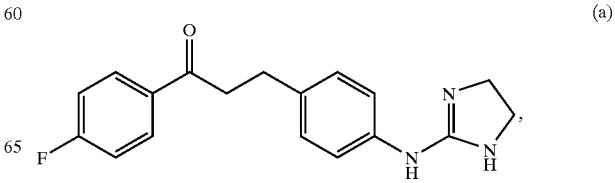

19. A pharmaceutical composition comprising a therapeutically effective amount of at least one compound of claim 1 in admixture with at least one pharmaceutically acceptable carrier.

20. The pharmaceutical composition of claim 19 wherein the at least one compound is suitable for administration to a subject having a disease state which is alleviated by treatment with an IP receptor antagonist.

21. A method of treating a subject having a disease state associated with pain, inflammation, urinary tract disease state, respiratory states from allergies or asthma, edema formation, or hypotensive vascular diseases, comprising administering to the subject a therapeutically effective amount of at least one compound of claim 1.

22. The method of claim 21 wherein the disease state is associated with pain.

23. The method of claim 22 wherein the disease state associated with pain is inflammatory pain, neuropathic pain, cancer pain, acute pain, chronic pain, surgical pain, dental pain, premenstrual pain, visceral pain, pain due to burns, migraine or cluster headaches, neuralgias, post traumatic injuries, pain is associated with functional bowel disorders such as irritable bowel syndrome, hyperalgesia, or complex regional syndromes.

24. The method of claim 21 wherein the disease state associated with inflammation.

25. The method of claim 24 wherein the disease state is associated with inflammation is bacterial, fungal infections, viral infections, idiopathic bladder inflammation, over-use, old age, nutritional deficiencites, prostatis, or conjunctivitis pain.

26. The method of claim 21 wherein the disease state is associated with urinary tract disease state.

27. The method of claim 21 wherein the disease state is associated with urinary tract disease state is bladder outlet obstruction, urinary incontinence, reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urge incontinence, urethritis, prostatitis, pelvic pain syndrome, prostatodynia, cystitis, or idiophatic bladder hypersensitivity.

28. The method of claim 21 wherein the disease state is associated with respiratory disease states from allergies or asthma.

29. The method of claim 21 wherein the disease state is associated with edema formation or hypotensive vascular diseases.

* * * * *